(12) United States Patent
Gong et al.

(10) Patent No.: US 7,468,350 B2
(45) Date of Patent: Dec. 23, 2008

(54) GLUE COMPOSITION FOR LUNG VOLUME REDUCTION

(75) Inventors: Glen Gong, San Francisco, CA (US); Ronald Dieck, Palo Alto, CA (US)

(73) Assignee: PNEUMRX, Inc., Mountain View, CA (US)

( * ) Notice: Subject to any disclaimer, the term of this patent is extended or adjusted under 35 U.S.C. 154(b) by 0 days.

(21) Appl. No.: 11/008,580

(22) Filed: Dec. 8, 2004

(65) Prior Publication Data

US 2005/0281801 A1 Dec. 22, 2005

Related U.S. Application Data

(60) Provisional application No. 60/586,950, filed on Jul. 8, 2004, provisional application No. 60/586,932, filed on Jul. 8, 2004, provisional application No. 60/580,444, filed on Jun. 16, 2004.

(51) Int. Cl.
*A61K 38/00* (2006.01)
*C07K 14/00* (2006.01)

(52) U.S. Cl. .................... 514/2; 514/12; 424/94.3; 424/178.1; 435/218

(58) Field of Classification Search ............. 514/2, 514/12; 424/94.3, 178.1; 435/218
See application file for complete search history.

(56) References Cited

U.S. PATENT DOCUMENTS

| | | | |
|---|---|---|---|
| 3,527,841 A | 9/1970 | Wicker, Jr. et al. | |
| 3,559,652 A | 2/1971 | Banitt et al. | |
| 3,722,599 A | 3/1973 | Robertson et al. | |
| 3,940,362 A | 2/1976 | Overhults | |
| 3,995,641 A | 12/1976 | Kronenthal et al. | |
| 4,418,052 A | 11/1983 | Wong | |
| 4,656,254 A | 4/1987 | Shearer et al. | |
| 5,008,245 A | 4/1991 | Digenis et al. | |
| 5,011,686 A | 4/1991 | Pang | |
| 5,024,829 A | 6/1991 | Berger et al. | |
| 5,162,307 A * | 11/1992 | Digenis et al. ............. 530/331 |
| 5,219,895 A | 6/1993 | Kelman | |
| 5,283,173 A | 2/1994 | Fields et al. | |
| 5,312,331 A | 5/1994 | Knoepfler | |
| 5,328,687 A | 7/1994 | Leung et al. | |
| 5,385,606 A | 1/1995 | Kowanko | |
| 5,478,925 A | 12/1995 | Wallach et al. | |
| 5,484,401 A | 1/1996 | Rodriguez et al. | |
| 5,514,371 A | 5/1996 | Leung et al. | |
| 5,514,372 A | 5/1996 | Leung et al. | |
| 5,549,904 A | 8/1996 | Juergensen et al. | |
| 5,575,997 A | 11/1996 | Leung et al. | |
| 5,582,834 A | 12/1996 | Leung et al. | |
| 5,583,114 A | 12/1996 | Barrows et al. | |
| 5,663,299 A | 9/1997 | Remold-O'Donnell | |
| 5,667,973 A | 9/1997 | Fields et al. | |
| 5,736,132 A | 4/1998 | Juergensen et al. | |
| 5,739,288 A | 4/1998 | Edwardson et al. | |
| 5,750,657 A | 5/1998 | Edwardson et al. | |
| 5,827,672 A | 10/1998 | Remold-O'Donnell | |
| 5,928,611 A | 7/1999 | Leung | |
| 5,981,621 A | 11/1999 | Clark et al. | |
| 6,010,714 A | 1/2000 | Leung et al. | |
| 6,087,325 A | 7/2000 | Meers et al. | |
| 6,183,498 B1 | 2/2001 | Devore et al. | |
| 6,287,290 B1 | 9/2001 | Perkins et al. | |
| 6,310,036 B1 | 10/2001 | Browdie | |
| 6,310,166 B1 | 10/2001 | Hickey et al. | |
| 6,329,337 B1 | 12/2001 | Morita et al. | |
| 6,352,716 B1 | 3/2002 | Janoff et al. | |
| 6,372,229 B1 | 4/2002 | Ollerenshaw et al. | |
| 6,375,926 B1 | 4/2002 | Barnes et al. | |
| 6,494,896 B1 | 12/2002 | D'Alessio et al. | |
| 6,500,461 B2 | 12/2002 | Perkins et al. | |
| 6,512,023 B1 | 1/2003 | Malofsky et al. | |
| 6,514,522 B2 | 2/2003 | Domb | |
| 6,552,172 B2 | 4/2003 | Marx et al. | |
| 6,565,842 B1 * | 5/2003 | Sojomihardo et al. ...... 424/85.1 |
| 6,685,626 B2 | 2/2004 | Wironen | |
| 6,734,006 B2 | 5/2004 | Xiao et al. | |
| 6,753,164 B2 | 6/2004 | Ni et al. | |

(Continued)

FOREIGN PATENT DOCUMENTS

EP 0367514 A2 5/1990

(Continued)

OTHER PUBLICATIONS

Belorgey, Dider et al. 1998. Effect of polynucleotides on the inhibition of neutrophil elastase by mucus protainase inhibitor and $\alpha_1$-proteinase inhibitor. *Biochemistry* 37(46): 16416-16422.

(Continued)

*Primary Examiner*—Chih-Min Kam
(74) *Attorney, Agent, or Firm*—Townsend and Townsend and Crew LLP

(57) ABSTRACT

The present invention relates to methods and compositions for sealing localized regions of damaged lung tissue to reduce overall lung volume. The glue compositions provide a glue featuring an adhering moiety coupled to one or more other moieties including, for example, a cross-linkable moiety and/or one other adhering moiety. The methods and compositions of the invention find use, for example, in treating pulmonary conditions, such as emphysema.

2 Claims, 2 Drawing Sheets

U.S. PATENT DOCUMENTS

| | | | |
|---|---|---|---|
| 6,774,216 | B2 | 8/2004 | Ruben et al. |
| 6,784,153 | B1 | 8/2004 | Rajotte et al. |
| 6,790,185 | B1 | 9/2004 | Fisher et al. |
| 6,830,756 | B2 | 12/2004 | Hnojewyj |
| 6,849,262 | B2 | 2/2005 | Ollerenshaw et al. |
| 2001/0031948 | A1 | 10/2001 | Cruise et al. |
| 2001/0047187 | A1 | 11/2001 | Milo et al. |
| 2002/0022588 | A1 | 2/2002 | Wilkie et al. |
| 2002/0071843 | A1 | 6/2002 | Li et al. |
| 2002/0086842 | A1 | 7/2002 | Plank et al. |
| 2002/0086852 | A1 | 7/2002 | Cantor et al. |
| 2002/0106411 | A1 | 8/2002 | Wironen et al. |
| 2002/0147462 | A1 | 10/2002 | Mair et al. |
| 2002/0161399 | A1 | 10/2002 | Cruise et al. |
| 2002/0176893 | A1 | 11/2002 | Wironen et al. |
| 2002/0183244 | A1 | 12/2002 | Ollerenshaw et al. |
| 2003/0017150 | A1 | 1/2003 | Torphy |
| 2003/0064050 | A1 | 4/2003 | Malik et al. |
| 2003/0070682 | A1 | 4/2003 | Wilson et al. |
| 2003/0070683 | A1 | 4/2003 | Deem et al. |
| 2003/0075170 | A1 | 4/2003 | Deem et al. |
| 2003/0100921 | A1 | 5/2003 | Addis et al. |
| 2003/0109866 | A1 | 6/2003 | Edwards et al. |
| 2003/0113369 | A1 | 6/2003 | Martin et al. |
| 2003/0138481 | A1 | 7/2003 | Zadi |
| 2003/0191496 | A1 | 10/2003 | Edwards et al. |
| 2003/0194797 | A1 | 10/2003 | Young et al. |
| 2003/0199440 | A1 | 10/2003 | Dack et al. |
| 2003/0216321 | A1 | 11/2003 | Lawrence et al. |
| 2003/0224430 | A1 | 12/2003 | Xiao |
| 2003/0232019 | A1 | 12/2003 | Basu et al. |
| 2003/0232048 | A1 | 12/2003 | Yang et al. |
| 2004/0009122 | A1 | 1/2004 | Klaveness et al. |
| 2004/0009217 | A1 | 1/2004 | Martin et al. |
| 2004/0030262 | A1 | 2/2004 | Fisher et al. |
| 2004/0043407 | A1 | 3/2004 | Chen et al. |
| 2004/0047855 | A1 | 3/2004 | Ingenito |
| 2004/0048302 | A1 | 3/2004 | Chen et al. |
| 2004/0049187 | A1 | 3/2004 | Burnett et al. |
| 2004/0063613 | A1 | 4/2004 | Rolke et al. |
| 2004/0072756 | A1 | 4/2004 | Wilkie et al. |
| 2004/0081648 | A1 | 4/2004 | Afeyan et al. |
| 2004/0086896 | A1 | 5/2004 | Carman et al. |
| 2004/0087778 | A1 | 5/2004 | Feige et al. |
| 2004/0106633 | A1 | 6/2004 | Lu et al. |
| 2004/0120849 | A1 | 6/2004 | Stewart et al. |
| 2004/0120979 | A1 | 6/2004 | Roessler et al. |
| 2004/0121362 | A1 | 6/2004 | Whiitney et al. |
| 2004/0124185 | A1 | 7/2004 | Patel et al. |
| 2004/0126777 | A1 | 7/2004 | Bhatt et al. |
| 2004/0172058 | A1 | 9/2004 | Edwards et al. |
| 2004/0176801 | A1 | 9/2004 | Edwards et al. |
| 2004/0225254 | A1 | 11/2004 | Tanaka et al. |
| 2004/0234575 | A1 | 11/2004 | Horres et al. |
| 2005/0004599 | A1 | 1/2005 | McNally-Heintzelman et al. |
| 2005/0281739 | A1 | 12/2005 | Gong et al. |
| 2005/0281740 | A1 | 12/2005 | Gong et al. |
| 2005/0281787 | A1 | 12/2005 | Gong et al. |
| 2005/0281796 | A1 | 12/2005 | Gong et al. |
| 2005/0281798 | A1 | 12/2005 | Gung et al. |
| 2005/0281799 | A1 | 12/2005 | Gong et al. |
| 2005/0281800 | A1 | 12/2005 | Gong et al. |
| 2005/0281802 | A1 | 12/2005 | Gong et al. |
| 2005/0282748 | A1 | 12/2005 | Gong et al. |
| 2005/0288549 | A1 | 12/2005 | Mathis |
| 2005/0288550 | A1 | 12/2005 | Mathis |
| 2005/0288684 | A1 | 12/2005 | Aronson et al. |
| 2005/0288702 | A1 | 12/2005 | McGurk et al. |
| 2006/0004400 | A1 | 1/2006 | McGurk et al. |
| 2006/0009748 | A1 | 1/2006 | Mathis |
| 2006/0009801 | A1 | 1/2006 | McGurk et al. |
| 2006/0025815 | A1 | 2/2006 | McGurk et al. |
| 2006/0167416 | A1 | 7/2006 | Mathis et al. |

FOREIGN PATENT DOCUMENTS

| | | |
|---|---|---|
| EP | 0529719 A1 | 3/1993 |
| EP | 1070049 B1 | 1/2001 |
| EP | 1378518 A1 | 1/2004 |
| EP | 1433486 A1 | 6/2004 |
| WO | WO 96/10418 A1 | 4/1998 |
| WO | WO 98/64446 A1 | 12/1999 |
| WO | WO 00/17227 A1 | 3/2000 |
| WO | WO 02/072751 A2 | 9/2002 |
| WO | WO 02/072769 A2 | 9/2002 |
| WO | WO 02/072788 A2 | 9/2002 |
| WO | WO 03/010327 A2 | 2/2003 |
| WO | WO 03/064639 A1 | 8/2003 |
| WO | WO 03/090682 A2 | 11/2003 |
| WO | WO 2004/001060 A2 | 12/2003 |
| WO | WO 2004/020620 A1 | 3/2004 |
| WO | WO 2004/031235 A1 | 4/2004 |
| WO | WO 2004/031253 A1 | 4/2004 |
| WO | WO 2004/045634 A1 | 6/2004 |
| WO | WO 2004/052236 A2 | 6/2004 |
| WO | WO 2004/054556 A1 | 7/2004 |
| WO | WO 2004/053117 A2 | 8/2004 |

OTHER PUBLICATIONS

Chambers, Rachel C. et al. 1998. Cadmium inhibits proteoglycan and Procollagen production by cultured human lung fibroblasts. *American Journal of Respiratory Cell and Molecular Biology* 19: 498-506.

Cho, Raymond J. et al. 1998. Parallel analysis of genetic selections using whole genome oligonucleotide arrays. *Proceedings of the National Academy of Science of the United States of America*, 95: 3752-3757.

Covault, H. Patrick et al. 1982. Liquid-chromatographic measurement of elastin. *Clinical Chemistry* 28(7): 1465-1468.

Cuvelier, A. et al. 2000. Inter-alpha tripsin inhibitor (ITI) proteins: an important role in the extracellular matrix *Rev. Mal. Respir.* 17: 437-446.

De Roos, Albert et al. 1991. Myocardial infarct sizing and assessment of reperfusion by magnetic resonance imaging: a review *International Jounal of Cardiac Imaging* 7(2): 133-138.

Duration, Jerome et al. 2003. Inhibition of proteinase 3 by $\alpha_1$-antitrypsin in vitro predicts very fast inhibition in vivo. *American Journal of Respiratory Cell and Molecular Biology* 29: 57-61.

Eng, Jibah et al. 1990. Successful closure of bronchopleural fistula with adhesive tissue. *Scand J Thor Cardiovasc Surg* 24(2): 157-59.

Felici, Franco et al. 1991. Selection of antibody ligands from a large library of oligopeptides expressed on a multivalent exposition vector. *Journal of Molecular Biology* 222(1): 301-310.

Francis, Gillian E. 1992. Protein modification and fusion proteins. *Focus on Growth Factors* 3: 4-10, Royal Free Hospital School of Medicine, London, Uk.

Fromont-Racine, Micheline et al. 1997. Toward a functional analysis of the yeast genome through exhaustive two-hybrid screens. *Nature Genetics* 16: 277-282.

Fujiwara, Yasuyuki. 2004. Cell biological study on abnormal proteoglycan synthesis in vascular cells exposed to heavy metals. *Journal of Health Science* 50(3): 187-204.

Gennaro, A.R. (Edit.) 1985: *Remington's Pharmaceutical Sciences*, Easton: Mack Printing Company.

Harper, J. Wade et al. 1993. The p21 cdk-interacting protein cip 1 is a potent inhibitor of G1 cylin-dependent kinases. *Cell* 75(4): 805-816.

Hermanson, Greg T. 1996. *Bioconjugate Techniques*. San Diego: Academic Press, Inc.

Inaspettato, G. et al. 1994. Endoscopic treatment of bronchopleural fistulas using n-butyl-2-cyanoacrylate. *Surgical Laparoscopy & Endoscopy* 4(1): 62-64.

Ingenito, Edward P. et al. 2001. Brochoscopic volume reduction: a safe and effective alternative to surgical therapy for emphysema. *American Journal of Respiratory and Critical Care Medicine* 164: 295-301.

Ingenito, Edward P. et al. 2003. Bronchoscopic lung volume reduction using tissue engineering principles. *American Journal of Respiratory and Critical Care Medicine* 167: 771-778.

Irving, James A. et al. 2000. Phylogeny of the serpin superfamily: implications of patterns of amino acid conservation for structure and function. *Genome Research* 10(12): 1845-1864.

Ito, Satoru et al. 2004. Tissue heterogeneity in the mouse lung: effects of elastase treatment. *Journal of Applied Physiology* 97(1): 204-212. available as an APS Article in PresS Mar. 12, 2004.

Janoff, Aaron. 1985. State of the art: elastases and emphysema—current assessment of the protease-antiprotease hypothesis. *American Review of Respiratory Disease* 132(2): 417-433.

Laurell, C.B. et al.1963. The electrohoretic $\alpha_1$-globulin pattern of serum in $\alpha_1$-antitrypsin deficiency. *Scandinavian Journal of Clinical and Laboratory Investigation* 15: 132-140.

Menache, M.G. et al. 1995. Particle inhalability curves for humans and small laboratory animals. *The Annals of Occupational Hygiene* 39(3):317-328.

Oldenburg, Kevin R. et al. 1992. Peptide ligands for a sugar-binding protein isolated from a random peptide library. *Proceedings of the National Academy of Sciences of the United States of America* 89(12): 5393-5397.

Osakabe, Toru et al. 1995. Comparison of ELISA and HPLC for the determination of desmosine or isodesmosie in aortic tissue elastin. *Journal of Clinical Laboratory Analysis* 9(5): 293-298.

Parmley, Stephen F. et al. 1988. Antibody-selectable filamentous fd phage vectors: affinity purification of target genes. *Gene*, 73(2): 305-318.

Powers, William J. et al. 1982. Indium-111 platelat scintigraphy in cerebrovascular disease. *Neurology* 32: 938-943.

Raabe, Otto G. 1982. Comparison of the criteria for sampling 'inhalable' and 'respirable' aerols. *Ann Occup. Hyg.* 26(1-4): 33-45.

Raabe, Otto G. et al. 1982. Studies of the chronic inhalation of coal fly ash by rats. *Ann. Occup. Hyg.* 26(1-4): 189-211.

Rajotte, Daniel et al. 1999. Membrane dipeptidase is the receptor for a lung-targeting peptide identified by in vivo phage display. *The Journal of Biological Chemistry* 274(17): 11593-11598.

Rowe, Raymond C., et al. 2003. *Handbook of Pharmaceutical Excipients* 4th Edition , London: Pharmaceutical Press.

Senior, Robert M. et al. 1988, Chapter 74: the pathogenesis of emphysema. *Pulmonary Diseases and Disorders*, Second Edition, 2: 1209-1218. New York: McGraw-Hill Book Company.

Sifers, Richard N. et al. 1989. Genetic control of human alpha-1-antitrypsin. *Molecular Biology and Medicin* 6: 127-135.

Starcher, Barry C. 2000. Lung elastin and matrix. *Chest* 117(5): 229S-234S.

Starcher, Barry et al. 1995. A role for neutrophil elastase in the progression of solar elastosis. *Connective Tissue Research* 31(2): 133-140.

Stone, Philip J. et al. 1991. Measurement of urinary desmosine by isotope dilution and high performace liquid chromatography. *American Review of Respiratory Disease* 144(2): 284-290.

Suki, Bela et al. 2003. On the progressive nature of emphysema. *American Journal of Respiratory and Critical Care Medicine* 168: 516-521.

Swanson, Scott J. et al. 1997. No-cut thoracoscopic lung plication: a new technique for lung volume reduction surgery. *Journal of the American College of Surgeons* 185(1): 25-32.

Thakur, Matthew L. et al. 1976. Indium-Ill labeled platelets: studies on preparation and evaluation of in vitro and in vivo functions. *Thrombosis Research* 9: 345-357.

The United States Pharmacopeia, 29th Revision. 2006. The United States Pharmacopelal Convention.

Valadon, Philippe. et al. 1998. Peptide libraries define the fine specificity of anti-polysaccharide antibodies to *Crytococcus neoformans*. *J. Mol. Biol.* 261: 11-22.

Westerink, M.A. Julie et al, 1995. Peptide mimicry of the meninfococcal group C capsular polysaccharide. *Proceedings of the National Academy of Sciences of the United States of America* 92(9): 4021-4025.

Wong, Shan S. 1991. *Chemistry of Protein Conjugation and Cross-Linking*. Boca Raton: CRC Press, Inc.

Zimmerman, Morris et al. 1989. Chapter 12: design and properites of synthetic elastase inhibitors. *Elastin and Elastases* 2: 109-123. Boca Raton: CRC Press, Inc.

Mathis, M., U.S. Appl. No. 11/286,445 entitled "Steerable Device for Accessing a Target Site and Methods", filed Nov. 23, 2005.

McGurk, E. et al., U.S. Appl. No. 11/178,243 entitled "Lung Device With Sealing Features", filed Jul. 8, 2005.

Moser, et al. Biologic half-life and organ distribution of radiolabeled human PiM and Piz alpha-1-antitrypsin in the dog. J Lab Clin Med. 1978; 91(2):214-22.

Moser, et al. Intravenous administration of alpha-1-proteinase inhibitor in patients of PiZ and PiM phenotype. Preliminary report. Am J Med. 1988; 84(6A):70-4.

\* cited by examiner

GLUE COMPOSITION FOR LUNG VOLUME REDUCTION

RELATED APPLICATIONS

This application claims priority to provisional applications U.S. 60/580,444, entitled "Targeting Damaged Lung Tissue," filed Jun. 16, 2004; U.S. 60/586,932, entitled "Targeting Damaged Lung Tissue Using Various Formulations," filed Jul. 8, 2004; and U.S. 60/586,950, entitled "Lung Volume Reduction Using Glue Composition," filed Jul. 8, 2004, each of which is incorporated herein in its entirety.

BACKGROUND OF THE INVENTION

Pulmonary conditions affect millions of Americans and many more individuals worldwide. Chronic obstructive pulmonary disease (COPD), for example, including emphysema, asthma, bronchiectais and chronic bronchitis, is one of the most common chronic conditions and the fourth leading cause of death in the United States. While various environmental and genetic factors may contribute to COPD, cigarette smoking is the primary cause. Cigarette smoke can trigger inflammatory responses within the lungs, activating elastase, cathepsin G, and matrix metalloproteinases (MMPs). These enzymes are proteases that result in progressive destruction of the elastic tissue of the lungs, reducing the elasticity and lung recoil required for exhalation. Damaged alveolar walls can eventually rupture to form inelastic "blebs." Emphysema, for example, is characterized by abnormal enlargement of alveolar airspaces distal to terminal bronchioles and destruction of airspace parenchyma resulting in such "blebs."

Current treatments are wanting. Treatment of pulmonary conditions often involves control and management rather than a cure for the disease. With emphysema, for example, treatment can involve cessation of smoking, exercise programs, medications that help open constricted airways, anti-inflammatory medications, oxygen therapy, placement of one-way valves, and lung volume reduction surgery (LVRS). LVRS involves surgical removal of damaged, over-inflated lung tissue to free up space for the expansion of remaining non-damaged tissue. This technique, however, requires invasive procedures and benefits tend to decline over time. Further, treatments using one-way valves have not proved satisfactory. Thus, there remains a need for improved methods for treating pulmonary conditions, such as emphysema.

The present invention provides methods and compositions directed thereto. Other methods and compositions directed thereto are provided in U.S. nonprovisional applications entitled "Targeting Damaged Lung Tissue Using Compositions," filed Dec. 8, 2004; "Targeting Damaged Lung Tissue," filed Dec. 8, 2004; "Targeting Sites of Damaged Lung Tissue Using Composition," filed Dec. 8, 2004; "Targeting Sites of Damaged Lung Tissue," filed Dec. 8, 2004; "Imaging Damaged Lung Tissue Using Compositions," filed Dec. 8, 2004; "Imaging Damaged Lung Tissue," filed Dec. 8, 2004; "Glue Compositions for Lung Volume Reduction," filed Dec. 8, 2004; "Lung Volume Reduction Using Glue Compositions," filed Dec. 8, 2004; and "Lung Volume Reduction Using Glue Composition," filed Dec. 8, 2004, each of which is herein incorporated in its entirety.

BRIEF SUMMARY OF INVENTION

One aspect of the invention relates to a glue composition comprising a first adhering moiety and a second adhering moiety where the adhering moieties are coupled and where the adhering moieties adhere different sites of lung tissue. In some embodiments, the lung tissue comprises epithelial lining fluid. In some embodiments, the different sites comprise different sites within an enlarged air space. In some embodiments, the first and second adhering moieties are the same. In some embodiments, the first and second adhering moieties are different.

In some embodiments, the adhering moieties are coupled via a chemical linker. In some embodiments, the chemical linker comprises two functional groups. In some embodiments, at least one of the functional groups is a hydroxyl group, a carboxyl group, an ester group, an amine group, or a lysine group. In some embodiments, at least one of the functional groups is a cyano group, a thiol group, a cysteine group, a carbonyl group, an aldehyde group or a ketone group. In some embodiments, the adhering moieties are coupled as a fusion polypeptide. In some embodiments, the adhering moieties are coupled via a protein. In some embodiments, the adhering moieties are coupled via an antibody. In some embodiments, the glue composition does not comprise a polysaccharide or a carbohydrate moiety. In some embodiments, the glue composition does not comprise a mutant plasminogen activator-inhibitor type 1.

In some embodiments, the adhering moiety adheres a cell surface marker. In some embodiments, the adhering moiety adheres an ECM component. In some embodiments, the first and/or second adhering moiety adheres elastase. In some embodiments, the first and/or second adhering moiety adheres neutropil elastase. In some embodiments, the first and/or second adhering moiety comprises a protease inhibitor moiety. For example, in some embodiments, the first and/or second adhering moiety comprises an alpha-1 antitrypsin moiety, for example, a recombinant alpha-1 antitrypsin moiety. In some embodiments, the first and/or second adhering moiety comprises an elafin moiety, for example, a recombinant elafin moiety. In some embodiments, the first and/or second adhering moiety comprises a serpin moiety, for example, a recombinant serpin moiety, a secretory leukoprotease inhibitor (SLP1) moiety, and/or a recombinant secretory leukoprotease inhibitor (SLP1) moiety. In some embodiments, the first and/or second adhering moiety adheres at least one matrix metalloproteinase selected from MMP-1, MMP-2, MMP-3, MMP-4, MMP-5, MMP-6, MMP-7, MMP-8, and MMP-9. In some embodiments, the glue composition does not comprise a hyaluronic acid or a salt thereof. In some embodiments, the first and/or second adhering moiety adheres desmosine and/or isodesmosine. In some embodiments, the first and/or second adhering moiety adheres CD8 and/or CD4. In some embodiments, the first and/or second adhering moiety adheres a smoke-related moiety.

In some embodiments, the glue composition is less than 10 microns. In some embodiments, the glue composition is less than 5 microns. In some embodiments, the glue composition is less than 1 micron.

In another aspect of the invention, the glue composition further comprises a cross-linkable moiety coupled to the first and/or second adhering moieties.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates one embodiment of a method to reduce lung volume using a glue composition comprising a cross-linkable moiety coupled to an adhering moiety that adheres to lung tissue.

FIG. 2 illustrates one embodiment of a method to reduce lung volume using a glue composition comprising coupled adhering moieties that adhere to different sites of lung tissue.

DETAILED DESCRIPTION OF THE INVENTION

Figure 1A:
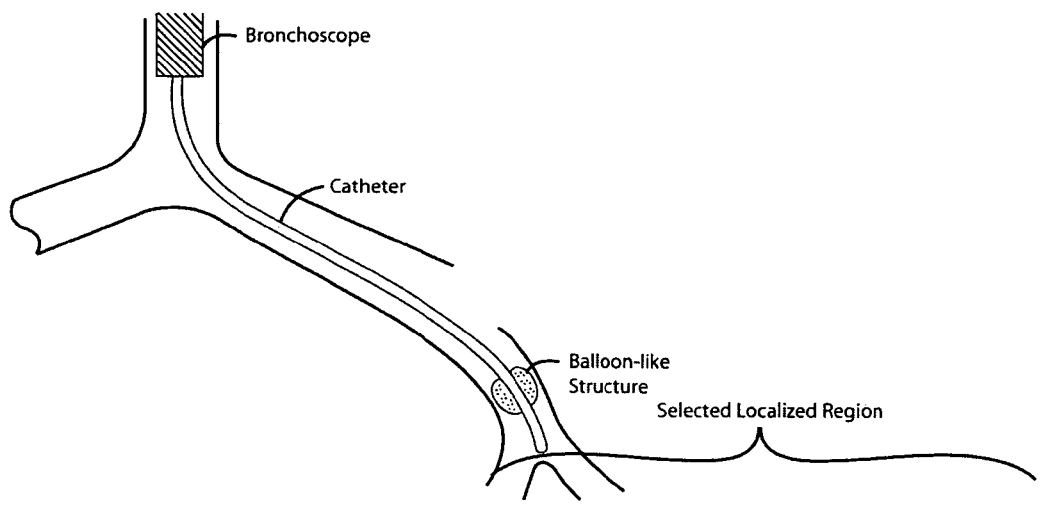
FIG. 1a schematically illustrates a bronchoscope placed in a bronchus from which a catheter extends to a segmental and subsegmental bronchus.
Figure 1B:
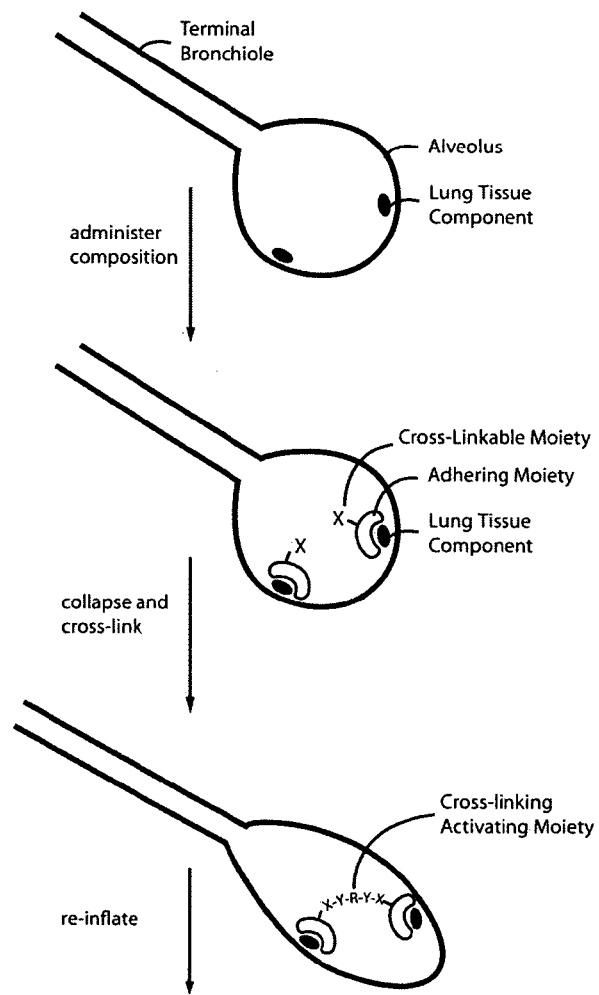
FIG. 1b schematically illustrates a terminal bronchiole, terminating in the airspace of an alveolus.

One aspect of the present invention provides a glue composition comprising an adhering moiety that adheres lung tissue, including lung fluids, such as, for example, epithelial lining fluid. An adhering moiety may adhere to lung tissue, for example, sites of non-diseased or normal lung tissue, as well as sites of diseased and/or non-normal lung tissue that may be affected, have been affected, or are likely to be affected by a pulmonary condition. An adhering moiety may bind, attach, or otherwise couple to lung tissue by covalent and/or non-covalent binding. Examples of binding forces that may be useful in the present invention include, but are not limited to, covalent bonds, dipole interactions, electrostatic forces, hydrogen bonds, hydrophobic interactions, ionic bonds, and/or van der Waals forces.

In some preferred embodiments, the adhering moiety adheres to a protease or other molecule and/or macromolecule present in lung tissue. For example, the adhering moiety may adhere a molecule and/or macromolecule found attached, bound, coupled, complexed and/or otherwise associated with lung tissue. Binding, attachment, coupling, complexing and/or association may involve covalent and/or non-covalent interactions, including, e.g., dipole interactions, electrostatic forces, hydrogen bonds, hydrophobic interactions, ionic bonds, and/or van der Waals forces.

In some embodiments, the adhering moiety may adhere a molecule and/or macromolecule that is bound, attached, coupled, complexed and/or otherwise associated with a cell surface of lung tissue. In some embodiments, the molecule and/or macromolecule may be bound to a cell wall. In some embodiments, the molecule and/or macromolecule may be complexed with a moiety that is itself bound to a cell wall. In some embodiments, the molecule and/or macromolecule may comprise a cell surface marker. In still some embodiments, the molecule and/or macromolecule may be found associated with the extra cellular matrix (ECM). For example, the molecule and/or macromolecule may comprise an ECM component or may be associated with an EMC component of lung tissue.

In some embodiments, the adhering moiety may adhere a molecule and/or macromolecule comprising at least one moiety selected from a protein moiety, a glycoprotein moiety, a lipoprotein moiety, a lipid moiety, a phospholipid moiety, a carbohydrate moiety, a nucleic acid moiety, a modified nucleic acid moiety, and/or a small molecule moiety, including, e.g., a cell surface marker comprising a glycoprotein moiety and/or an ECM component comprising a protein moiety.

In some preferred embodiments, the adhering moiety adheres to elastase. The elastase may be bound to the cell wall and/or associated with the extracellular matrix of lung tissue. For example, elastase causes progressive destruction of elastic fibers of lung tissues in some pulmonary conditions, e.g., emphysema, resulting in dilation and rupture of distended alveoli to form characteristic "blebs." Suki et al., "On the Progressive Nature of Emphysema, Pulmonary Perspective", *American Journal of Respiratory and Critical Care Medicine*, Vol. 168 pgs. 516-520 (2003); Janoff et al., *Am. Rev. Respir. Dis., Vol.* 132 pgs. 417-433 (1985); Senior and Kuhn, In Fishman (ed), *Pulmonary Diseases and Disorders,* 2d ed. New York, McGraw-Hill, p. 1209-1218 (1988). In some preferred embodiments, the adhering moiety adheres to neutrophil elastase and/or neutrophils. In some preferred embodiments, the adhering moiety adheres pancreatic and/or macrophage elastase. In some preferred embodiments, the adhering moiety adheres neutrophil proteinase 3 (Pr3). Pr3 is descried, for example, in Duranton et al., "Inhibition of proteinase 3 by alpha-1 antitrypsin in vitro predicts very fast inhibition in vivo", *Am J Respir Cell Mol. Biol.*, Vol. 29 No. 1 pgs 57-61 (2003).

For example, the adhering moiety may (or may not) comprise alpha-1 antitrypsin, elafin, thypin (see, e.g., International Publication No. WO 02/072769), and/or other serpin, e.g., PAI-1, PAI-2, SCCA-1, SCCA-2, secretory leukoprotease inhibitor SLP-1, (see, e.g., U.S. Pat. No. 6,753,164), and/or other serpin-related proteins (e.g., as disclosed in U.S. Publication No. 2004/0126777); a recombinant form of any of these and/or a moiety of any of these that retains the ability to adhere to lung tissue. In some embodiments, the adhering moiety may (or may not) comprise mucous proteinase inhibitor (MPI) that shows high affinity for binding to elastase. Belorgey et al., "Effect of polynuclotides on the inhibition of neutrophil elastase by mucus proteinase inhibitor and alpha-1 proteinase inhibitor", *Biochemistry*, Vol. 37 No. 46 pgs 16416-22 (1998). Other adhering moieties that can adhere to elastase may also be used, such as inhibitors of elastase known in the art. See, e.g., Janoff et al., *Am. Rev. Respir. Dis.* Vol. 132 pgs 417-433 (1985); Zimmerman and Powers (1989), In Hornebeck (ed), *Elastin and Elastases*, vol II, Boca Raton, CRC Press, pgs 109-123; and Laurell and Eriksson *Scand. J. Clin. Lab. Invest.*, Vol. 15 pgs 132-140 (1963). Other adhering moieties can include protease inhibitors of the inter-alpha trypsin inhibitor (ITI) family. The ITI protein family can be built up from different combinations of the polypeptides HC1, HC2, HC3 and bikunin, as described, e.g., in Cuvelier et al., "Proteins of the inter-alpha trypsin inhibitor (ITI) family. A major role in the biology of the extracellular matrix", *Rev Mal Respir.*, Vol. 17 No. 2 pgs 437-46 (2000).

Alpha-1 antitrypsin useful for preparing an adhering moiety of the present invention may be obtained by any techniques known in the art and/or disclosed herein. For example, alpha-1 antitrypsin can be obtained by recombinant methods, as known in the art (e.g., recombinant alpha-1 antitrypsin from Novartis). Techniques for purifying alpha-1 antitrypsin, e.g., from biological natural and/or recombinant sources are also known in the art. See, e.g., International Publication No. WO 00/17227 and U.S. Pat. No. 4,656,254, which describes separating alpha-1 antitrypsin from plasma.

In some preferred embodiments, the adhering moiety adheres to desmosine and/or isodesmosine. Desmosine and/or isodesmosine are amino acids produced as a result of damage to lung tissues, particularly damage involving destruction of elastin. Fragmented elastin, for example, is metabolized to free desmosine or small peptides, which can be recovered in the urine of the subject. See, e.g., Starcher B.

C., "Lung Elastin and Matrix", *Chest*, Vol. 117 pgs 229S-234S (2000). In animal models of emphysema, for example, desmosine urine recovery can serve as a measure of lung damage. There are several micromethods for measuring desmosine, including, for example, enzyme-linked immunosorbent assay (see, e.g., Osakabe T. et al. "Comparison of ELISA and HPLC for the determination of desmosine and isodesmosine in aortic tissue elastin", *J. Clin Lab Anal Vol.* 9 pgs 293-296 (1995)); isotope dilution (see, e.g., Stone P. J. et al. "Measurement of urinary desmosine by isotope dilution and high performance liquid chromatography", *Am Rev Respir Dis* Vol. 144 pgs 284-290 (1991)); high performance liquid chromatography (see, e.g., Covault H. P. et al. "Liquid-chromatographic measurement of elastin", *Clin Chem* Vol. 28 pgs 1465-1468 (1982)); and/or radioimmunoassay (see, e.g., Starcher B. "A role for neutrophil elastase in the progression of solar elastosis", *Connect Tissue Res* Vol. 31 pgs 133-140 (1995)).

In some preferred embodiments, the adhering moiety adheres to cathepsin, e.g., cathepsin G, which can be produced by inflammatory cells in the pathogenesis of COPD. In some embodiments, the adhering moiety adheres other cysteine proteinases. In some embodiments the adhering moiety adheres cathepsins L, S, and K. In some embodiments, the adhering moiety adheres RGS2, which accumulates at sites of macrophage activation, e.g., in activated-macrophage-related disorders, including emphysema. See, e.g., EP 1378518. In some embodiments, the adhering moiety adheres to alveolar macrophages. In some embodiments, the adhering moiety adheres to eosinophils. In some embodiments, the adhering moiety adheres to tumor necrosis factor-α. In some embodiments, the adhering moiety adheres to kallikrenin.

In some preferred embodiments, the adhering moiety adheres a collagenase. The presence of collagenase activity may be detected, for example, by released components, e.g., amino acids, known to occur in collagen, e.g., hydroxyproline and/or hydroxylysine.

Examples of collagenases include, e.g., one or more metalloproteinases. Metalloproteinases include, e.g., MMP-1 (interstitial collagenase or collagenase-1), MMP-2 (gelatinase-A or 72 kD gelatinase), MMP-3 (transin, human fibroblast stromelysin or stromelysin-1), MMP-4, MMP-5, MMP-6, MMP-7 (matrilysin), MMP-8 (collagenase-2 or neutrophul collagenase), MMP-9 (gelatinase B or 92 kD gelatinase), MMP-10 (stromelysin II), MMP-11 (stromelysin III), MMP-12 (macrophase metalloelastase), and/or MMP-13 (collagenase-3) and as well as metalloproteinase ADAM 2222 (see, e.g., U.S. Publication No. 2003/0194797). Metalloproteinases (also referred to as metalloproteases in the art) have been described, e.g., U.S. Publication No. 2003/0199440; U.S. Publication No. 2004/0048302; U.S. Publication No. 2004/0043407; U.S. Publication No. 2003/0194797; and International Publication No. WO 02/072751. For example, an adhering moiety comprising an ilomastat moiety may be used. See, e.g., International Publication No. WO 2004/052236.

In some embodiments, the glue composition does not comprise a polysaccharide or carbohydrate moiety, e.g., in some embodiments, the glue composition does not comprise hyaluronic acid or a salt thereof; and in some embodiments, the glue composition does not comprise dextran or glycosaminoglycan. In some embodiments, the glue composition does not comprise a polysaccharide or carbohydrate moiety that binds to elastic fibers. In some embodiments, the glue composition does not comprise an antibody. In some embodiments, the glue composition does not comprise a lung membrane dipeptidase-binding molecule, e.g., in some embodiments, the glue composition may not adhere to lung membrane dipeptidase, and in some embodiments the glue composition may not comprise GFE-1 peptide. See, e.g., Rajotte, et al., "Membrane dipeptidase is the receptor for a lung-targeting peptide identified by in vivo phage display", *J Biol Chem* Vol. 274 No. 17 pgs 11593-8(1999) and U.S. Pat. No. 6,784,153.

Also, in some preferred embodiments, the adhering moiety adheres to CD8 and/or CD4, CD8 lymphocytes and/or CD4 lymphocytes, and/or interleukin 8 (see, e.g., U.S. Publication No. 2003/0232048). In some embodiments, the adhering moiety adheres to mitogen-activated protein kinase (International Publication No. WO 03/064639). In some embodiments, the adhering moiety may (or may not) adhere to CIRL-2 homologs (see, e.g., International Publication No. WO 2004/031235). In still some embodiments, the adhering moiety may (or may not) comprise an antibody and/or binding fragment thereof that adheres to lung tissue. For example, the adhering moiety may comprise a COPD-related human Ig derived protein, discussed e.g. in International Publication No. WO 02/072788 and/or U.S. Publication No. 2003/0017150, which can bind COPD related proteins. In yet another example, the adhering moiety may comprise an antibody to secreted protein HCEJQ69 (see, e.g., U.S. Pat. No. 6,774,216).

Preferred adhering moieties of the present invention comprise biological moieties, such as proteins or polypeptides, which can adhere to lung tissue, and can include naturally-occurring protease inhibitors, such as alpha-1 antitrypsin and/or mutants thereof and/or fragments thereof, as well as other protease inhibitor moieties. As well as alpha-1 antitrypsin, other naturally-occurring inhibitors of elastase may also be used as preferred adhering moieties of the present invention, including, e.g., monocyte elastase inhibitor and variants thereof (see, e.g., International Publication No. WO 96/10418; U.S. Pat. Nos. 5,827,672; and 5,663,299); as well as tissue inhibitors of metalloproteinases (TIMPs), such as TIMP-1, TIMP-2, TIMP-3, and TIMP-4.

In more preferred embodiments, the adhering moiety is modified such that it binds to lung tissue irreversibly, substantially irreversibly, or at least with a high binding constant, e.g., to resist dissociation for a desired period of time. Adhering moieties may be selected and/or developed to increase binding affinity for lung tissue. For example, alpha-1 antitrypsin may be mutated by random and/or directed synthesis, to engineer mutants with higher binding constants for elastase. For example, in some preferred embodiments, the adhering moiety has a $K_i$ value against a component of lung tissue of less than about 200 nM, less than about 150 nM, less than about 100 nM, or less than about 75 nM. In some preferred embodiments, the adhering moiety has a $K_i$ value against a component of lung tissue of more than about 50 nM, more than about 25 nM, more than about 20 nM, more than about 15 nM, more than about 10 nM, more than about 5 nM, more than about 3 nM, or more than about 1 nM. In some preferred embodiments, the adhering moiety binds a component of lung tissue with a $K_D$ less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M.

Other non-naturally occurring protease inhibitors that may (or may not) be used as an adhering moiety of the present invention include inhibitors of neutrophil elastase (e.g., methyl ketone derivatives); inhibitors of macrophage metalloproteinase (e.g., RS113456 and inhibitors discussed in U.S. Publication No. 2003/0199440); Cathepsin G inhibitors (e.g., LEX-032 (Sparta)); various elastase inhibitors (e.g.ABT-491

(Abbot)); inhibiting compositions (e.g., as disclosed in U.S. Publication No. 2003/0199440 and International Publication No. WO 03/090682, including lipase inhibitors and phospholipase inhibitors); protease inhibitor compositions (e.g., as disclosed in International Publication No. WO 2004/045634); Erdosteine (Edmond Pharma), FK-706 (Fujisawa), GW-311616 (Glaxo-Wellcome), Midesteine (Medea); a mutant plasminogen activator-inhibitor type 1 (see, e.g., U.S. Publication No. 2003/0216321); an N-substituted azetidinone (see, e.g., EP 0529719); peptidyl carbamates (e.g., U.S. Pat. No. 5,008,245 and/or EP 0367514); SR-268794 (Sanoti) and/or SYN-1134 (Syn. Pharm.); other proteinase inhibitors (e.g., CMP-777 (Dupont)); heteroaryl aminoguanidines and alkoxyguanidines (see, e.g., U.S. 2004/0106633 and EP 1070049); as well as ON-elastase inhibitors (e.g., NX-21909 (Gilead)); and several HNE inhibitors (e.g., CE-1037 (Cortech/United Ther), CE-2000 series (Cortech/Ono), EPI-HNE-4 (Dyax), EPI-HINE-1 (Protein Engineer), MDL-101146 (HMR), Ono-5046 (Ono), SPAAT (UAB Res. Found.), WIN-63759 (Sterling Winthrop), ZD-8321 (AstraZeneca), and/or ZD-0892 (AstraZeneca)). Adhering moieties may (or may not) also include inhibitors and/or antibodies of any lung tissue components described herein, as well as inhibitors and/or antibodies of proteins described in International Publication No. WO 03/010327; as well as inhibitors and/or antibodies of eosinophul seine protease 1-like enzymes described in U.S. Publication No. 2003/0224430 and/or other seine proteases, e.g., described in International Publication No. WO 2004/053117; as well as inhibitor and/or antibodies of transmembrane serine proteases, e.g., as discussed in U.S. Pat. No. 6,734,006; as well as inhibitors and/or antibodies of esterase described in International Publication No. WO 04/020620. As used herein, "antibodies" includes binding fragments thereof.

In some preferred embodiments, the adhering moiety comprises a compound, such as a small molecule compound, that adheres lung tissue or a component thereof. Such compounds can be obtained, for example, via ligand screening methods, as known in the art. For example, a biological sample or a defined candidate moiety can be brought into contact with a component of lung tissue, for example purified and/or recombinant elastase, or fragments thereof, as well as a component isolated and/or purified from epithelial lining fluid. The candidate moiety may be labeled with a detectable label, such as a fluorescent, radioactive, and/or an enzymatic tag and allowed to contact the lung tissue component that may be immobilized, e.g., under conditions that permit binding. After removing unbound moieties, bound moiety can be detected using appropriate methods as known in the art.

Candidate moieties that can be assayed for adhering lung tissue for use in the present invention are not limited. For example, such candidate moieties can be obtained from a wide variety of sources including libraries of synthetic, semi-synthetic and/or natural substances. Random and/or directed synthesis can be used, for example, to generate a wide variety of organic compounds and biomolecules, including randomized oligonucleotides and oligopeptides. With respect to natural compounds, libraries form bacterial, fungal, plant and animal extracts are available and/or can be readily produced. Further, natural, semi-synthetically, and/or synthetically produced libraries can be modified through conventional chemical, physical, recombinant, and/or biochemical techniques to produce combinatorial libraries. Also, known pharmaceutical or pharmacological agents may be modified by directed or random chemical modifications, including, for example, acylation, amidification, alkylation, and/or esterification to produce structural analogs.

Candidate moieties may include natural, synthetic and/or semi-synthetic organic compounds, macromolecules of biological origin, such as polypeptides, peptides, polysaccharides, glycoproteins, lipoproteins, fatty acids, and/or fragments thereof; and/or drugs or small molecules, such as molecules generated through combinatorial chemistry approaches. Further, when the candidate moiety comprises a peptide or polypeptide, the candidate moiety may be expressed by a phage clone belonging to a phage-based random peptide library (see, e.g., Parmley and Smith, *Gene* Vol. 73 pgs 305-318 (1988); Oldenburg et al., *Proc. Natl. Acad. Sci. USA* Vol. 89 pgs 5393-5397(1992); Valadon et al., *J. Mol. Biol.*, Vol. 261 pgs 11-22 (1996); Westerink, *Proc. Natl. Acad. Sci USA.*, Vol. 92 pgs 4021-4025 (1995); and Felici et al., *J. Mol. Biol.*, Vol. 222 pgs 301-310) (1991); and/or the candidate moiety may be expressed from a cDNA cloned in a vector for performing a two-hybrid screening assay (U.S. Pat. Nos. 5,667,973 and 5,283,173; Harper et al., *Cell*, Vol. 75 pgs 805-816 (1993); Cho et al., *Proc. Natl. Acad. Sci. USA*, Vol. 95(7) pgs 3752-3757 (1998); and Fromont-Racine et al., *Nature Genetics*, Vol. 16(3) pgs 277-282 (1997).

The adhering moiety may also adhere to a smoke-related moiety. For example, the adhering moiety may bind to cigarette smoke particles, tar, tobacco, and/or other smoke-related residues, such as Cadmium. Further, it is to be understood that the adhering moiety may adhere one of more components of lung tissue and/or smoke-related moieties, including any combination of proteases disclosed herein, as well as one or more proteases and/or one or more smoke-related moieties.

In some embodiments, the adhering moiety may adhere to modified polypeptides. For example, members of the G-protein coupled receptor (GPCR) family, e.g., RAI-3 are modified, e.g., phosphorylated, and/or associated with tyrosine phosphorylated activation complexes following exposure to cigarette smoke. See, e.g., International Publication No. WO 04/001060 and/or U.S. Publication No. 2004/0121362. In some embodiments of the present invention, an adhering moiety may be used that adheres to such modified proteins and/or protein complexes. Such adhering moieties may (or may not) include modulators of RAI-3, as described in U.S. Publication No. 2004/0121362. In still some embodiments, an adhering moiety may (or may not) be used that adheres polypeptides associated with the NF-kB pathway that are found in lung tissue, e.g., as described in U.S. Publication No. 2004/0086896.

The adhering moiety may also adhere moieties that inhibit the production of elastic and/or connective tissue proteins. Such moieties may include, e.g., moieties that inhibit fibroblast proliferation and/or that inhibit procollagen production and/or that inhibit proteoglycan synthesis, preferably moieties that inhibit synthesis of the major matrix-associated proteoglycans, such as versican, decorin, and/or large heparan sulfate proteoglycans. "Inhibiting" and its various grammatical conjugations can mean reducing a biological process, e.g., reducing synthesis of a connective tissue component, by an amount compared with the occurrence of the process in the absence (or in the presence of lower levels) of the inhibiting moiety. In some embodiments, the amount may be reduced by at least about 10%, at least about 20%, at least about 30%, at least about 40%, or at least about 50%. In some embodiments, the amount may be reduced by less than about 60%, less than about 70%, less than about 80%, less than about 90%, or less than about 95%. "Inhibiting" and its various grammatical conjugations need not mean completely inhibiting a biological process, e.g., it need not mean inhibiting synthesis of a connective tissue component to negligible and/or non-detectable levels. Moieties that can inhibit proteoglycan synthesis include, for example, Cadmium. See, e.g., Chambers et al., "Cadmium inhibits proteoglycan and procollagen production by cultures human lung fibroblasts," *Am. J. Respir. Cell Mol. Biol.*, Vol. 19 No. 3 pgs 498-506 (1998). Other moieties may include lead, aldehydes and/or silicates. Fujiwara, "Cell biological study on abnormal proteoglycan synthesis in vascular cell exposed to heavy metals," *Journal of Health Science*, Vol. 50 No. 3 pgs 197-204 (2004). The adhering moiety may also adhere to moieties that impair the repair of elastic and/or connective tissues of the lungs.

In some aspects of the present invention, a glue composition comprising an adhering moiety also comprises a cross-linkable moiety coupled thereto. The cross-linkable moiety can be any moiety that facilitates linkage between more than one cross-linkable moieties, preferably between cross-linkable moieties coupled to adhering moieties binding to lung tissue at different sites. Cross-linkable moieties can include, for example, a hydroxyl group, carboxyl group, ester group, cyano group, thiol group (including e.g., a cysteine group), carbonyl group, aldehyde group, ketone group, primary amine group, and/or secondary amine group, as well as a lysine group.

In some embodiments, the cross-linkable moiety comprises any other amine groups, a sulfide group, a carbonyl group (e.g., α-halocarbonyl group and/or α,β-unsaturated carbonyl group), a cyanate group (e.g., isothiocyanate group), a carboxylate group (e.g., an acetate group such as α-haloacetate group), a hydrazine group, and/or a biotin group. See, e.g., US Publication No. 2002/0071843.

In some embodiments, the cross-linkable moiety can comprise fibrinogen and/or fibrin. Fibrinogen can be converted to fibrin, which is polymerized in a cross-linking reaction. In some embodiments, the cross-linkable moiety can comprise other protein and/or proteinaceous materials, e.g., proteinaceous materials comprising albumin (bovine or human), collagen, PEI, oleic acid, chitin and/or chitosan, as well as any of those described in U.S. Pat. Nos. 5,385,606, 5,583,114, 6,310,036, 6,329,337, and/or 6,372,229. In some embodiments, more than one type of cross-linkable moiety may be coupled to a given adhering moiety or may be coupled to a number of adhering moieties used in combination, e.g., in one administration or in a number of successive administrations. Those of skill in the art will recognize other suitable cross-linkable moieties that may be used in the practice of the instant invention, including, for example, any biocompatible cross-linkable moiety that can form a biocompatible cross-linked product.

The adhering moiety may be coupled to the cross-linkable moiety by any techniques and/or approaches known in the art, described herein, and/or as can be developed by those of skill in the art. For example, coupling methods include, but are not limited to the use of bifunctional linkers, amide formation, imine formation, carbodiimide condensation, disulfide bond formation, and/or use of a specific binding pair e.g., using a biotin-avidin interaction. These and other methods known in the art may be found, e.g., in Hermanson, "Bioconjugate Techniques," Academic Press: San Diego 1996; and S. S. Wong, "Chemistry of Protein Conjugation and Cross-linking," CRC Press, 1993.

In preferred embodiments, the cross-linkable moiety is coupled to the adhering moiety in such a way so as not to interfere with the ability of the adhering moiety to adhere to lung tissue. For example the cross-linkable moiety can be attached to an alpha-1 antitrypsin moiety at one or more sites that do not modify the conformation or folding of the alpha-1 antitrypsin, or do not modify the conformation or folding of regions of alpha-1 antitrypsin necessary and/or involved in adhering to sites of lung tissue, e.g. adhering to elastase present in lung tissue. For example, without being limited to a given hypothesis or mode of action, the active inhibitory site of alpha-1 antitrypsin is found around Ser358 of the polypeptide, e.g., forming a pseudo-irreversible equimolar complex with neutrophil elastase. See, e.g., Sifers et al., "Genetic Control of Human Alpha-1 Antitrypsin", *Mol. Biol. Med*, Vol. 6 pgs 127-135 (1989). In some preferred embodiments, a cross-linkable moiety can be attached to an alpha-1 antitrysin moiety at a site other than around its Ser358 inhibitory site. Similarly, in some embodiments, without being limited to a given hypothesis or mode of action, a cross-linkable moiety can be attached to a serpin moiety at a site other than certain regions known to be involved in attaching to a protease, which include, for example, the hinge, breach, shutter, and gate regions of serpins. Irving et al., *Genome Res* Vol. 10 pgs 1845-64 (2000). Similarly, in some embodiments, without being limited to a given hypothesis or mode of action, a cross-linkable moiety can be attached to a monocyte elastase inhibitor moiety at a site other than a cysteine residue of the inhibitor involved in interacting with elastase and/or proteinase 3 and/or cathepsin G. See, e.g., International Publication WO 96/10418; and U.S. Pat. No. 5,827,672.

In some embodiments, the cross-linkable moiety may be chemically bound to the adhering moiety, e.g., a carboxyl group covalently attached to one or more sites of alpha-1 antitrypsin. In some embodiments, the cross-linkable moiety may be chemically bound to a moiety that is itself chemically bound to the adhering moiety, indirectly coupling the cross-linkable and adhering moieties.

In preferred embodiments, the size of the glue composition comprising an adhering moiety coupled to a cross-linkable moiety is not so large as to prevent access of the glue f composition to lung tissue within enlarged alveoli distal to a terminal bronchiole. For example, the size of the glue composition comprising an adhering moiety coupled to a cross-linkable moiety is preferably less than about 10 microns, less than about 8 microns, less than about 5 microns, less than about 3 microns, less than about 2 microns, or less than about 1 micron. "Enlarged alveolus" as used herein refers to an alveolus that is larger than the average alveolus that is not affected by a pulmonary condition, or that is affected to a lesser extent. For example, an enlarged alveolus may be at least about 5%, at least about 10%, at least about 20%, at least about 50%, at least about 100%, or at least about 150% the size of an average alveolus.

Another aspect of the present invention relates to a glue composition comprising a first adhering moiety and a second adhering moiety wherein said adhering moieties are coupled and wherein said adhering moieties adhere to different sites of lung tissue. In preferred embodiments, the different sites comprise different sites within an enlarged air space, e.g., within alveolar walls of an over-inflated alveolus distal to a terminal bronchiole, as characteristic of some pulmonary conditions, including emphysema. The first and second adhering moieties may be the same or different.

Further, it is to be understood that any plural number of adhering moieties may be used, i.e., the present invention also contemplates a glue composition comprising any plural number of coupled adhering moieties, that may each be the same or different, or some may be the same while others are different. For example, in a glue composition comprising three coupled adhering moieties, the first adhering moiety may be coupled to the second adhering moiety, which is coupled to a third adhering moiety. The first and third moieties may or may not be directly coupled to each other. In some embodiments, the three adhering moieties may be coupled to a moiety without being directly coupled to each other. The three moieties may all be the same or different, or two may be the same with the third is different. Each adhering moiety may adhere to the same of different components in lung tissue, preferably adhering at different sites within an enlarged air space, e.g., within alveolar walls of an over-inflated alveolus distal to a terminal bronchiole.

The adhering moieties may be coupled by any techniques and/or approaches known in the art, described herein, and/or as can be developed by those of skill in the art. In some embodiments, coupling may involve covalent bonds, dipole interactions, electrostatic forces, hydrogen bonds, hydrophobic interactions, ionic bonds, van der Waals forces, and/or other bonds that can couple adhering moieties. For example, in some embodiments, adhering moieties are coupled via a coupling moiety, e.g., a chemical linker. Any chemical linker may be used, including, e.g., an aliphatic group covalently linking the adhering moieties. For example, a chemical linker useful in this invention may comprise two (or more) functional groups, where each of the functional groups can be chemically bonded to an adhering moiety, serving to couple the adhering moieties. Examples of functional groups include, e.g., a hydroxyl group, a carboxyl group, an ester group, a cyano group, a thiol group, a cysteine group, a carbonyl group, an aldehyde group, a ketone group, and/or an amine group, as well as a lysine group. Other function groups include a cyanate group (e.g., isothiocyanate) and/or a carboxylate group (e.g., an acetate group such as α-haloacetate).

Other coupling techniques may also be used. For example, dimers and/or multimers of adhering moieties may be prepared using cross-linking techniques so that the adhering moieties are pre-cross-linked, e.g., forming one or more cross-links between cysteine residues of peptide and/or polypeptide adhering moieties. Linker length optimization techniques may also be used (see, e.g., U.S. Pat. No. 5,478, 925), for use in the present invention.

In some embodiments, adhering moieties are coupled as a fusion polypeptide. For example, where the adhering moieties are peptides and/or polypeptides, two or more adhering moieties may be joined by a polypeptide linker as the coupling moiety, to form a fusion polypeptide or fusion protein. A fusion protein may be generated in various ways, including, e.g., chemical coupling and co-translation. In some preferred embodiments, adhering moieties are recombinantly expressed as a fusion product from a recombinant nucleic acid molecule, where the adhering moieties are linked, e.g., by one or more intervening amino acids, according to techniques known in the art. See, e.g., Francis, “Focus on Growth Factors”, Vol. 3 pgs 4-10 (Mediscript, London) (1992). Fusion proteins may also be made using other techniques known in the art, e.g., techniques used to create adzymes, which comprise an address binding site conjugated to a catalytic domain (e.g., as described in U.S. Publication No. 2004/0081648 and in U.S. Publication No. 2004/0081648); and/or by covalent linking (e.g., via disulfide bonds) between at least one amino acid of each coupled adhering moiety (e.g., as descried in U.S. Publication No. 2004/0087778).

In some embodiments, the adhering moieties are coupled via a protein, e.g., an antibody and/or a binging fragment thereof. In some embodiments, liposomes may be prepared that comprise a plural number of adhering moieties.

In some preferred embodiments, the adhering moieties are coupled in such a way so as not to interfere with the ability of the adhering moiety to adhere lung tissue. For example two (or more) alpha-1 antitrypsin moieties can be coupled to each other at sites that do not modify the conformation or folding of the alpha-1 antitrypsin moieties, or do not modify the conformation or folding of regions of the alpha-1 antitrypsin moieties necessary and/or involved in adhering to sites of lung tissue, e.g. adhering to elastase present in lung tissue. For example, without being limited to a given hypothesis or mode of action, the active inhibitory site of alpha-1 antitrypsin is found around Ser358 of the polypeptide, e.g., forming a pseudo-irreversible equimolar complex with neutrophil elastase. See, e.g., Sifers et al., “Genetic Control of Human Alpha-1 Antitrypsin”, *Mol. Biol. Med.*, Vol. 6 pgs 127-135 (1989). In some preferred embodiments, alpha-1 antitrysin moieties may be coupled to each other or other adhering moieties at sites other than around their Ser358 inhibitory sites. Similarly, in some embodiments, without being limited to a given hypothesis or mode of action, serpin moieties may be coupled to each other or other adhering moieties at sites other than certain regions known to be involved in attaching to protease, which include, for example, the hinge, breach, shutter, and gate regions of serpins. Irving et al., *Genome Res* Vol. 10 pgs 1845-64 (2000). Some serpins, for example, contain a reactive center loop (RCL) involved in inhibition where a stable complex can be formed between the protease and a cleaved form of the serpin. Attachment via sites other than the RCL regions of serpin moieties is preferred in some embodiments. Similarly, in some embodiments, without being limited to a given hypothesis or mode of action, monocyte elastase inhibitor moieties can be coupled to each other or other adhering moieties at a site other than a cysteine residue of the inhibitor involved in interacting with elastase and/or proteinase 3 and/or cathepsin G. See, e.g., International Publication WO 96/10418 and U.S. Pat. No. 5,827,672.

In preferred embodiments, the size of the glue composition comprising two (or more) coupled adhering moieties is not so large as to prevent access of the glue composition to sites of lung tissue within enlarged air spaces distal to a terminal bronchiole. For example, the size of the glue composition comprising two (or more) adhering moieties is preferably less than about 10 microns, less than about 8 microns, less than about 5 microns, less than about 3 microns, less than about 2 microns, or less than about 1 micron.

Coupling of the adhering moieties can keep the adhering moieties in close or relatively close physical proximity. For example, in some preferred embodiments a chemical linker may be used that comprises an aliphatic group of at least about 2 carbon atoms, at least about 5 carbon atoms, at least about 10 carbon atoms, or at least about 12 carbon atoms. In some preferred embodiments, a chemical linker that comprises an aliphatic group of less than about 30 carbon atoms, less than about 20 carbon atoms, or less than about 15 carbon atoms can be used. In some preferred embodiments, a polypeptide linker can be used that comprises at least about one amino acid, at least about 3 amino acids, or at least about 5 amino acids. In some preferred embodiments, a polypeptide linker that comprises less than about 12 amino acids, less than about 10 amino acids, or less than about 5 amino acids can be used.

Further, it is to be understood that a glue composition comprising two (or more) coupled adhering moieties may further comprise a coupled or not coupled cross-linkable moiety.

Formulation, Routes of Administration, and Effective Doses

The glue compositions useful in the practice of the present invention can be delivered to a subject using a number of routes or modes of administration. The adhering moieties, cross-linkable moieties, cross-linking activating moieties, imaging moieties and/or other moieties and/or agents may be delivered per se or as pharmaceutically acceptable salts thereof. The term "pharmaceutically acceptable salt" means those salts which retain the biological effectiveness and desired properties of the moieties and/or agents of the present invention, and which are not biologically or otherwise undesirable. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the moiety contains a carboxyl group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

The adhering, cross-linkable, cross-linking activating, imaging moieties and/or other moieties and/or agents, or pharmaceutically acceptable salts thereof, can be formulated with a pharmaceutically acceptable carrier for administration to a subject in need thereof. "Pharmaceutically acceptable carriers" are well known in the pharmaceutical art, described, for example, in *Remington's Pharmaceutical Sciences*, Mack Publishing Co. (A. R. Gennaro edit. 1985). Suitable carriers include, for example, carriers like alcohol, DMSO, saline solution, and/or water. Pharmaceutical compositions for use in accordance with the present invention may be formulated in conventional manner using one or more physiologically acceptable carriers comprising excipients and/or auxiliaries, which facilitate processing of the active moieties into preparations that can be used pharmaceutically. Proper formulation is dependent upon the route of administration chosen.

In some embodiments, the glue compositions of the invention are dissolved in a suitable solvent, such as sterile water or PBS, and then dried to remove the solvent and produce a powder. Drying can be carried out in such as way as to retain the desired properties of the glue compositions, for example the capability of an adhering moiety to adhere lung tissue. For example, vacuum concentration, spray drying, open drying, freeze-drying, and the like, can be used. The residue obtained can then be ground and/or further micronized.

In some preferred embodiments, the adhering, cross-linkable, cross-linking activating and/or imaging moieties, or pharmaceutically acceptable salts thereof, as well as other moieties and/or agents and/or pharmaceutically acceptable salts thereof, are formulated as dry powders or aerosolized physiologically acceptable solutions that may be delivered to the lungs of a subject. Power and/or liquid formulations can be prepared to facilitate administration, e.g., to facilitate transfer from the delivery device into the respiratory tract, preferably down to the alveoli distal to terminal bronchiles.

Powder formulations can be prepared in various ways, using conventional techniques. Powder formulations can be processed to improve ability to be delivered to a subject, e.g., via inhalation and/or trans-thoracically. For instance, the way in which the formulation flows through and/or out of an inhaler device or other device, can be improved by forming spherical agglomerates by, e.g., dry granulation processing. Spherical agglomerate can impart the glue compositions of this invention with superior handling characteristics. It is to be understood, however, that the present invention contemplates the use agglomerates and/or other particles of all shapes, including both spherical and non-spherical shapes. Power and/or liquid formulations also preferably have physical characteristics that help avoid clogging of an aerosol device and clumping of aerosolized material. For example, additives such as alcohol, soaps, surfactants, and/or Vitamin E may be use to help reduce clumping and to facilitate formation of small particles and/or droplets.

Liquid formulations may be produced by adding a volume of sterile delivery solvent to an amount of sterile composition of the present invention in powder or liquid form. In some embodiments, formulation temperatures of at least about 0° C., at least about 4° C., at least about 5° C., at least about 10° C., or at least about 15° C. may be used. In some embodiments, formulation temperatures of less than about 100° C., less than about 80° C., less than about 60° C., less than about 37° C., or less than about 30° C. may be used.

Formulation of the present invention may also be prepared to provide other suitable physiological parameters for use in the lungs, including for example, suitable pH. For instance, a pH of at least about 4, at least about 5, or at least about 6 may be used. In some embodiments, a pH of less than about 11.0, less than about 10.0, less than about 9.0, less than about 8, or less than about 7 may be used.

In preferred embodiments, formulation involves selecting parameters such as concentration, size and/or viscosity of adhering, cross-linkable, cross-linking activating and/or imaging moieties, as well as of other moieties and/or agents, and/or pharmaceutically acceptable salts thereof, e.g., to provide a rheological profile, such that when aerosolized and/or nebulized, the formulation produces a range of particle and/or droplet sizes capable of being delivered to the lungs. A suitable mill, such as a jet mill, can be used to produce particles in a range of sizes that facilitates, or preferably maximizes, access to sites of damaged lung tissue, including sites distal to terminal bronchioles. In some embodiments, a nozzle comprising tapering pores may be used, e.g., to increase uniformity of the aerosol generated. See, e.g., U.S. Publication No. 2004/0124185.

In more preferred embodiments, a formulation is prepared that allows respiratory zone or deep lung delivery. In such embodiments, the formulation can yield a range of particle and/or droplet sizes adapted for delivery to the deep lung. In still more preferred embodiments, formulation involves selecting parameters such as concentration, size and/or viscosity of adhering, cross-linkable, cross-linking activating and/or imaging moieties, as well as of other moieties and/or agents and/or pharmaceutically acceptable salts thereof, such that when aerosolized and/or nebulized, the formulation produces a range of particle and/or droplet sizes capable of being delivered to the lung alveoli, preferably to a lung alveolus distal to a terminal bronchiole, and more preferably to the deepest terminal branches of selected lung segments.

Droplets and/or particles of suitable size ranges can be obtained by selecting appropriate delivery devices, molecular weight, concentration, and/or additives as known in the art and/or described herein. See, e.g., U.S. Publication No. 2002/0086842. For example, various glue formulations can be screened to determine ones that produce droplet and/or particle size in desired ranges.

In preferred embodiments, the glue compositions of the present invention are administered to a selected localized region of damaged lung tissue via the respiratory tract, e.g., via inhalation. The term "inhalation" includes inhalation via the mouth, nose, tracheae, or any combination thereof. A pharmaceutical formulation for administration via inhalation may be made up according to techniques known in the pharmaceutical arts and administered via aerosol inhalation, dry powder inhalation, liquid inhalation, and/or instillation. For example, a diagnostically and/or therapeutically effective amount of a glue composition of the invention may be delivered by inhalation of a breathable mist by the animal subject.

Preparation of inhalable formulations are known in the art, e.g., see U.S. Publication No. 2003/0232019 and International Publication No. WO 2004/054556. For example, a glue composition of the present invention can be formulated with a breathable fluorocarbon propellant. Inhalable preparations preferably provide droplets and/or particles with median mass distribution size of at least about 0.1 microns, at least about 0.3 microns, at least about 0.5 microns, at least about 1 micron, or at least about 2 microns. Inhalable preparations preferably provide droplets and/or particles with median mass distribution size of less than about 20 microns, less than about 15 microns, less than about 10 microns, less than about 6 microns, less than about 5 microns, less than about 3 microns, or less than about 2 microns. Particle and/or droplet sizes are preferably between about 2 microns to about 5 microns.

Size may be selected to allow glue compositions of the present invention access to sites of damaged tissue in selected lung regions. The respiratory system can be divided into three regions: (i) the tracheal/pharyngeal region, (ii) the bronchial region, and (iii) the alveolar region. Droplets and/or particles of about 10 microns to about 50 microns typically migrate to the tracheal/pharyngeal and/or bronchial region of the lungs; while droplets and/or particles of about 0.5 microns to about 5 microns, e.g., droplets and/or particles of about 2 microns, typically migrate to the alveolar region. Larger sizes may not as efficiently reach alveoli through distal bronchioles. Smaller droplets and/or particles may be exhaled by the subject before the adhering moiety contacts and/or adheres to lung tissue. Droplet and/or particle size of glue compositions of the present invention can be measured by techniques known in the art, including, e.g., those described herein.

Various physical parameters may be used to facilitate access of glue compositions of the present invention to selected localized sites of damaged tissue within the lungs. For example, the mass median aerodynamic diameter (MMAD), usually expressed in microns, can be used to predict where a droplet and/or particle distributes in the lungs. Mass Median Aerodynamic Diameter can be measured using a Cascade Impactor relating to size of compositions of the present invention. A humidified Cascade Impactor is preferably used to better reflect conditions of pulmonary delivery. Further, particle size distribution can also be measured with a Malvern Laser, for example. The geometric standard deviation (GSD) is another parameter that can be used. A GSD of about 1 correlates to a normal distribution. A GSD of less than about one can indicate a narrow size dispersion while a GSD of more than about 1 can indicate a broad size dispersion.

Charge may also be used to facilitate aerosol formation. For example, in some embodiments, droplets and/or particles can be made to carry a negative charge. The like charges can repel each other, helping to disperse the particles and/or droplets into an aerosol cloud by, e.g., by electrostatic forces. Like positive charges on particles and/or droplets may also be used in a similar manner.

Animal models can also be used to determine suitable ranges of droplet and/or particle size for delivery of glue compositions of the present invention to damaged lung tissue, e.g., see Raabe et al., "Studies of the Chronic Inhalation of Coal Fly Ash by Rats" *Ann. Occup. Hyg.* (1982), 26(1-4):189-211 (surveying access of particle size to various regions of the lungs in laboratory animals).

Solution or liquid formulations may be aerosolized to form a breathable mist via, e.g., a device such as an inhaler, a nebulizer, and/or an atomizer. In some embodiments, the formulation is a dry power, which can be made up into solution, e.g., with saline or water before aerosolization. In still some embodiments, a dry powder can be delivered per se by a device such as an intra alveolar device (IAD), an air gun powered aerosol chamber, and/or other dry powder delivery devices, e.g., from Dura Delivery Systems and/or Glaxo Wellcome.

A glue composition of the present invention may be aerosolized by any techniques known in the art, described herein and/or that can be developed. For example, the glue composition may be pressurized through micro pores and then blown through an inline blower, such as a high-pressure fan system. The fan or pump is preferably timed to coincide with the time of inspiration or a time just before inspiration. In some embodiments, for example, the delivery of the glue compositions can be metered as a function of the in-flow volume.

The aerosolized composition can be delivered by any methods known in the art and/or described herein. For example, the glue composition can be infused under pressure directly into a bronchus and/or into an enlarged air space. A catheter can be used to suck air out of a less distal lumen of the lungs through another path. In some embodiments, the glue composition can be infused into an enlarged air space using a first catheter while sucking air out with a second catheter through another path leading from the same air space, e.g., from another bronchi branch, to get a circular flow path. In yet another approach, the flow around a catheter or other infusion device can be blocked using balloons, covered braid structures, expanding foam, flaps that make one-way valves, and/or expanding corrugations.

Glue compositions of the present invention may also be administered via inhalation using a portable (e.g., hand held) inhaler device, such as devices used to deliver anti-asthmatic agents or anti-inflammatory agents. For example, a fine dry powder can be delivered as an aerosol by compressing air into the powder inside the inhaler. This can disperse the powder as a cloud of particles, preferably of the size ranges that allow access to alveoli distal to terminal bronchioles.

In some embodiments, the inhaler device may be designed to deliver single or multiple doses, minimizing risks from accidental large doses, and protecting the formulation from light, excessive moisture, and/or other contaminants. Dry powder and metered dose inhalers can be used to administer glue compositions of the invention to the pulmonary air passages of a subject in need thereof. Metered dose inhalers can deliver medicaments in a dispersion and/or in solubilized form. These inhalers can include a relatively high vapor pressure propellant, which forces aerosolized material into the respiratory tract upon activation of the device.

Some embodiments involve delivery by nebulization to the lungs, where, e.g., the delivery device can be a nebulizer. For example, a nebulizer can be used that generates an aerosol containing the glue compositions of the present invention, preferably an aerosol of droplets and/or particles of less than about 10 microns. Nebulizers are known in the art, and include, e.g., a jet nebulizer, which can be an air or liquid jet nebulizer; an ultrasonic nebulizer; a compressed air nebulizer (e.g., an AeroEclipse, Pari L. C., a Parijet; and/or a Whisper Jet) and/or a pressure mesh nebulizer. Compressed air nebulizers can generate droplets by using fast moving air to shatter a liquid stream. Ultrasonic nebulizers can nebulize a liquid solution using ultrasonic waves, e.g., by using a piezoelectric transducer to transform electrical current into mechanical oscillations; while pressure mesh nebulizers force fluid through a mesh-like surface under pressure. The nebulizer may use a pressure of at least about 5 psi, at least about 10 psi, at least about 15 psi, at least about 20 psi, at least about 25 psi, or at least about 30 psi. The nebulizer may use a pressure of less than about 60 psi, less than about 50 psi, or less than about 40 psi. For administration using a nebulizer, a subject can inhale aerosolized composition of the present invention via continuous neblulization, e.g., in a manner similar to that used to administer aerosolized bronchodilators. For example, the aerosol may be delivered via tubing or a mask to the mouth and/or nose, as well as by using an Ambu bag, blow-by mask, endotracheal tube, nasal cannula, nasal covering, and/or non-rebreather.

A suitable volumetric flow rate (L/min) for the nebulizer may be selected. It is preferable that the volumetric flow rate not exceed twice the subject's minute ventilation, as the average inspiratory rate is about twice the minute ventilation with exhalation and inhalation each representing about half of the breathing cycle. For example, a nebulizer with a volumetric flow rate of less than about 20 L/min, less than about 15 L/min or less than about 10 L/min may be used. A nebulizer can also be selected to generate desired ranges of particle and/or droplet size. Along with volumetric flow rate, various factors may be considered as will be appreciated by one of skill in the art. Such factors include aerosol mass output (mg/L) and/or retained volume (mL). For example, with respect to a compressed air nebulizers, factors such as air flow, hole diameter, and/or air pressure can influence size distribution. With respect to an ultrasonic nebulizer, factors include rate of air flow, hole diameter, and/or ultrasound frequency, Administration can also involve delivery of aerosolized droplets and/or powders of the present invention under positive pressure ventilation. For example, a device such as a Continuous Positive Airway Pressure device can be used to afford ventilatory assistance. This assistance can facilitate access of the glue compositions of the present invention to sites of damaged tissue in alveoli of the deep airways. Additionally, positive end expiratory pressure may be used to provide further assistance in this regard. In some embodiments, a device can be used that delivers a glue composition of the present invention when the subject produces a level of negative inspiratory pressure, e.g., at inspiratory flow rates.

Other devices that may be used include, for example, include a canister adapted to contain a preparation comprising a glue composition of the present invention under pressure. The canister may feature a valve, e.g., for regulating delivery of the preparation; a nozzle connected to the valve for converting the pressurized preparation inside the canister into an inhalable aerosol mist upon actuating the valve. See, e.g., U.S. Publication No. 2002/0086852. Other devices for delivery of glue compositions of the present invention to the lungs of a subject in need thereof include a spray atomizer.

Glue compositions of the present invention can also be delivered in a non-aerosolized form. Further, any combination of aerosol and/or non-aerosol forms may be used.

For example, a liquid, solution, suspension, viscous liquid, liquid film, slurry, foam, and/or thicksotropiec form(s) may be used. Any of such forms can be delivered to selected localized regions of the lungs by any techniques known in the art, to be developed, and/or described herein. For example, a liquid, solution, suspension, viscous liquid, liquid film, slurry, foam, and/or thicksotropiec form can be administered by fluid washings, liquid ventilation, bolus liquid drip and/or pulmonary lavage, e.g., to a selected region of damaged lung tissue. In some embodiments, a fluorochemical medium may be used.

Administered solutions may include, for example, physiologically acceptable solutions of adhering, cross-linkable, cross-linking activating and/or imaging moieties (and/or other moieties and/or agents) of the present invention. After delivery at a selected region of damaged lung tissue, the solvent can evaporate and/or dissipate such that the adhering moiety, cross-linkable moiety, cross-linking activating and/or imaging moiety (and/or other moiety and/or agent) is left behind.

In still some embodiments, the glue compositions may be delivered as solids, semi-solids, solid films, hydrogels, agars, and/or sol-gels. For example, glue compositions of the present invention may be administered to a selected localized region of the lungs as an absorbable sponge, e.g., as an absorbable gelatin sponge (e.g., GelfoaMTM) and/or as an absorbable wax. Non-absorbable waxes may also be used. Further, in some embodiments, petroleum-based compounds (e.g., petrolatum), latex, natural or synthetic rubber, starches, and/or alginate compounds may be used in formulating glue compositions of the present invention.

Aerosol and/or non-aerosol formulations can be delivered to a localized region of damaged lung tissue, preferably a localized region that has been selected for volume reduction. For example, a localized region of lung tissue showing a large portion of damaged alveoli, e.g., "blebs" or other damage due to a pulmonary condition, such as emphysema, can be selected. The region identified via radiology for diagnosis, e.g., can be located via bronchoscopy for treatment.

In some preferred embodiments, a bronchoscope is placed down the trachea of a subject (e.g., an anesthetized intubated patient) and into a bronchus, most preferably, as distally as possible to the selected region of damaged lung tissue. The anatomical site for administration, e.g., administration by a bronchoscope, may depend on the location and/or extent of lung tissue damage. Within the respiratory tree, segmental bronchi branch and/or subdivide to produce subsegmental bronchi, which in turn branch and/or subdivide to produce bronchioles that terminate in alveoli. The bronchoscope can be placed in the trachea and advanced towards the branching bronchi. The bronchoscope that may be used is not limited, and may include, e.g., a rigid or fiberoptic bronchoscope, e.g., a bronchoscope that allows visualization of an illuminated field. Use of an imaging moiety with a glue composition of the present invention can facilitate such visualization (e.g. using fluoroscopy), as discussed in more detail below. Bronchoscopes that may be used in the practice of the present invention include, for example, Fujinon, Olympus, and/or Pentax bronchoscopes.

A catheter can then be advanced through the bronchoscope, e.g., through the working channel of the bronchoscope. The catheter used is not limiting, but preferably comprises a small diameter catheter, having a diameter at least less than that of the working channel of the bronchoscope. The catheter can be a single or dual lumen catheter. The catheter can be advanced beyond the trachea and bronchi, e.g., to reach a segmental bronchus, a subsegmental bronchus, a bronchiole and/or an alveolus of the selected localized region of damaged lung tissue. The catheter can be allowed to become wedged in one or more of these segmental bronchi, subsegmental bronchi, bronchioles and/or alveoli, therein anchoring the distal tip of the catheter.

In some embodiments, the catheter used further comprises an expandable structure at and/or near its distal tip, e.g., a balloon or balloon-like structure. The expandable structure may be distended, e.g., with air, saline, any other suitable fluid and/or other medium, to assist, for example, in anchoring the tip of the catheter and/or positioning it for delivery of a glue composition of the present invention (in aerosol and/or non-aerosol form) to the selected localized region of damaged lung tissue. The balloon (or balloon-like structure) may be spherical, cylindrical, or any other shape. The distended balloon (or balloon-like structure) may have a diameter of at least about 0.1 mm, at least about 0.5 mm, at least about 1.0 mm, at least about 1.5 mm, at least about 3 m, at least about 4 mm, at least about 5 mm, at least about 6 mm, at least about 7 mm, at least about 8 mm, at least about 9 mm, or at least about 10 mm. The balloon diameter may be less than about 30 mm, less than about 20 mm, less than about 15 mm, or less than about 12 mm. The diameter selected can help position the balloon (or balloon-like structure) in a segmental bronchi, subsegmental bronchi, bronchiole and/or alveolus within a deep region of the lung. This anchoring and/or positioning can facilitate delivery of the glue composition of the present invention to the selected localized region of damaged lung tissue. A glue composition may then be administered in aerosol and/or non-aerosol forms, preferably at a controlled flow, to the selected localized region of damaged lung tissue. The inflated balloon (or balloon-like structure) may additionally help contain the administered glue composition to areas of the selected region of the lung that are distal to the balloon (or balloon-like structure). That is, the balloon (or balloon-like structure) can help prevent the administered glue composition from spreading to other regions of the lungs other than the selected localized regions of damaged lung tissue.

A number of administrations may be carried out before removal of the bronchoscope. For example, compositions containing additional moieties, e.g., a cross-linking activating moiety, a sclerosing agent, and/or any other moiety and/or agent, may also be administered at the same time or at separate times before removal. The balloon (or balloon-like structure) may then be deflated and withdrawn through the bronchoscope. In some embodiments, additional glue composition is administered after removal of the catheter, e.g., to seal any gap due to the physical location of the balloon (or balloon-like structure). See, e.g., Publication No. U.S. 2002/0147462. In some embodiments, glue composition is delivered by the catheter distal to the balloon (or balloon-like structure) so that no additional administration of glue composition is required.

As well as or instead of a catheter, forceps and/or other suitable instruments may be used to deliver glue compositions of the present invention to a selected localized region of damaged lung tissue. For example, an endotracheal tube and/or applicator may be used and/or, in some embodiments, administration may achieved by laproscopy. In less preferred embodiments, administration can be achieved by open surgery, e.g., by a thracotomy, but less-invasive procedures are preferred, as indicated above.

In some embodiments, glue compositions of the present invention are delivered to the lungs via instillation, e.g., direct instillation through the trachea, e.g., through the anterior aspect of the trachea. The glue compositions of the present invention can be administered as a liquid solution, including, e.g., an aqueous solution comprising water or a buffered physiological solution, such as saline. Instillation administration can be carried out over a period of at least about 2 minutes, at least about 5 minutes, at or least about 10 minutes. The instillation period may be less than about 30 minutes, less than about 20 minutes, or less than about 15 minutes. The length of instillation time may be selected based on a number of factors, including the glue composition used, the size of the selected region of damaged lung tissue to be treated, the extent of the damage, and the like. Instillation may involve delivery via bronchoscopy and/or endoscopy.

Other techniques for delivering glue compositions of the present invention to a selected localized region of damaged lung tissue may also be used, including, e.g., use of an impregnated applicator tip, e.g., U.S. Pat. No. 5,928,611; and/or an applicator for delivering liquid and/or semi-liquid compositions via laproscopy and/or endoscopy e.g., U.S. Pat. No. 6,494,896. Fibers, micro fibers, lattice-work stents, filagree designs, and/or porous structures may also be used, e.g., where the structure is coated with a glue composition of the present invention and delivered to a selected localized region of damaged lung tissue The glue compositions of the present invention can also be delivered via trans-thoracic administration. For example, in some embodiments, air spaces of selected damaged regions of lung tissue can be targeted directly through the ribs for more controlled localization, e.g., being applied through a scope. Trans-thoracic delivery may involve delivery into the pleural space using a needle percutaneously and/or using a catheter and/or chest tube. Glue compositions of the present invention can also be delivered to the lungs during liquid ventilation or pulmonary lavage using a fluorochemical medium.

The glue compositions of the present invention can also be given intravenously. For example, the pharmaceutical glue compositions of the present invention may be formulated with a pharmaceutically acceptable carrier to provide sterile solutions or suspensions for administration via injection. Injectables can be prepared in conventional forms, e.g., as liquid solutions, suspensions and/or solid forms suitable for making a solution or suspension in liquid prior to injection, and/or as emulsions. Suitable excipients that may be used include, for example, water, saline, dextrose, mannitol, lactose, lecithin, albumin, sodium glutamate, cysteine hydrochloride, and the like. In some embodiments, pharmaceutical compositions for injection may contain auxiliary substances, such as wetting agents, pH buffering agents, and the like. For example, a carbonate/bicarbonate buffer system may be used.

In some embodiments, the glue compositions of the invention are administered using a delivery vehicle. A "delivery vehicle" as used herein refers to any particle that can be used to carry compositions of the present invention. Examples of delivery vehicles include, but are not limited to, liposomes, viral, bacteriophage, cosmid, plasmid, and fungal vectors and other recombinant vehicles typically used in the art.

Delivery vehicles can carry a glue composition of the present invention encoded by a polynucleotide sequence. Expression of the sequence can produce the glue composition, e.g., a fusion polypeptide of two or more coupled adhering moieties. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to enhance in vitro transcription and/or expression, it may be necessary to remove, add, and/or alter 5' and/or 3' untranslated portions to eliminate extra, potentially inappropriate alternative translation initiation codons, or other sequences that may interfere with or reduce expression, either at the level of transcription or translation. In some embodiments, consensus ribosome binding sites can be inserted immediately 5' of the start codon to enhance expression.

In some embodiments, a viral vector can be used. A viral vector can include a natural or recombinantly produced virus or viral particle that comprises a polynucleotide to be delivered, either in vivo, ex vivo or in vitro. Examples of viral vectors include baculovirus vectors, retroviral vectors, adenovirus vectors, adeno-associated virus vectors and the like. A viral vector can enter a host cell via its normal mechanism of infection or can be modified such that it binds to a different host cell, e.g., by binding to a different surface receptor or ligand to enter the different host cell.

Delivery vehicles can also include non-viral vectors, including liposome complexes. Liposomes may comprise an aqueous concentric layer adherent to a hydrophopic or lipidic layer. The hydrophobic layer may comprise, for example, phospholipids, such as lecithin and sphingomyelin, steroids such as cholesterol, as well as ionic surface active substances such as dicetyphosphate, phosphatidic acid, stearylamine, and the like. Various liposome complexes known in the art may be used to aid delivery of the glue compositions of the invention to the lungs, in aerosol and/or non-aerosol formulation. For example, particulate formulations combining compounds having biocompatible hydrophobic domains with conjugates having both hydrophobic and hydrophilic regions may be used. See, e.g., U.S. Pat. No. 6,500,461. In some embodiments, lipid vesicles may be used comprising bilayers with a salt form of an organic acid derivative of a sterol, as described, e.g., in U.S. Pat. No. 6,352,716. In some embodiments, the use of liposome complexes can facilitate-delivery of glue compositions of the present invention, e.g., by keeping the glue composition intact and/or in appropriate conformation necessary and/or involved in adhering to lung tissue.

In still some embodiments, liposomes containing compositions of the invention are coated with, e.g., a hydrophilic agent, such as hydrophilic polymer chains like polyethylene glycol (PEG). Examples of PEG-liposomes are known in the art, e.g., see U.S. Publication No. 2003/0138481 and U.S. Publication No. 2003/0113369. In some embodiments, the adhering moiety may be coupled to exposed PEG chains to facilitate adhering to lung tissue. In some embodiments, the hydrophilic chains may temporarily shield the adhering moiety from interaction with lung tissue. Such liposomes are described, e.g., in U.S. Publication No. 2004/0009217.

In some embodiments, liposome complexes may facilitate selective delivery to localized regions of damaged lung tissue. For instance, peptide-lipid conjugates may be incorporated into liposomes, for example to selectively destabilize the liposomes in the vicinity of high amounts of elastase or other peptidases, as found in certain pulmonary conditions. See, e.g., peptide-lipid conjugates described in U.S. Pat. No. 6,087,325.

Delivery vehicles can also include other delivery systems associated with membranes (e.g., biocompatible or bioerodable membranes), including, e.g., dendrimer-based methods. See, e.g., U.S. Publication No. 2004/0120979. See also, e.g., U.S. Publication No. U.S. 2003/0064050, describing dendritic polymer conjugates useful as drug delivery systems. For example, a dentritic polymer conjugate useful as a delivery system in the practice of the present invention can comprise a dendritic polymer coupled to an adhering moiety described herein.

In some embodiments, a glue composition of the present invention may be used with a moiety that increases solubility and/or pharmacologic compatibility of the adhering, cross-linkable, cross-linking activating and/or imaging moiety, as well as other moieties and/or agents, for example, by enhancing hydrophobicity. For example, in some embodiments, absorption enhancing preparations (e.g., liposomes described above) may be utilized. Moieties that may be co-administered to achieve such effects include, for example, amphotericin B, betamethasone valerete, beclomethasone, cortisone, dexamethasone, DPPC/DPPG phospholipids, doxorubicin, estradiol, isosorbide dinitrate, nitroglycerin, prostaglandins, progesterone, testosterone, and/or vitamin E, and/or esters of any of these.

Glue compositions for use in treating pulmonary conditions preferably have low levels of toxicity during useable life and are preferably sterilized. Sterilization may be accomplished by techniques known to in the art, including, for example, chemical, physical, and/or irradiation methods. Physical methods can include sterile fill, filtration, use of heat (dry or moist) and/or retort canning. Irradiation methods of sterilization can include gamma irradiation, electron beam irradiation, and/or microwave irradiation. Preferred methods are dry and moist heat sterilization and electron beam irradiation. Different moieties of the invention can be sterilized separately, e.g., as described in EP 1433486, e.g., to form final sterile glue compositions.

Preferably, the glue compositions of the present invention have a bacterial count of less than about 2 cfu/g, less than about 1 cfu/g, or less than about 0.1 cfu/g. Such precautions can reduce abscess formation. Preservatives may also be used including, but not limited to, hydroquinone, pyrocatechol, resorcinol, 4-n-hexyl resoreinol, captan (i.e., $3\alpha,4,7,7\alpha$-tetrahydro-2-((trichloromethyl)thio)-1H-isoindole-1,3 (2H)-dione), benzalkonium chloride, benzalkonium chloride solution, benzethonium chloride, benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercurie nitrate and phenylmercuric acetate, formaldehyde, and formaldehyde generators such as the preservatives Germall II.RTM. and Germall 115.™. (imidazolidinyl urea, available from Sutton Laboratories, Charthan, N.J.), and the like. Further, preferred preparations contain nontoxic concentrations of toxins, such a heavy metals, for example, using established criteria for USP water for inhalation.

The present invention also encompasses pharmaceutical glue compositions prepared for storage before administration. Such compositions preferably contain preservatives and/or stabilizers. For example, sorbic acid and/or esters of phydroxybenzoic acid may be added. In addition, antioxidants and suspending agents may be used.

Pharmaceutical glue compositions useful in this invention may also include stabilizing agents, e.g., to reduce premature cross-linking. Stabilizing agents can include, e.g., vapor phase stabilizers, such as an anionic vapor phase stabilizer, and/or liquid phase stabilizers, e.g., an anionic liquid phase stabilizer. Such stabilizing agents may also include radical stabilizing agents, and/or a mixture of various stabilizing agents, preferably where the mixture does not interfere with, retard, and/or prevent the desired reaction. See, e.g., U.S. Pat. Ser. No. 6,512,023.

If necessary or desirable, the glue compositions of the present invention may be administered in combination with one or more other therapeutic agents. The choice of therapeutic agent that can be co-administered with a glue composition of the present invention will depend, in part, on the condition being treated and the desired effect to be achieved.

For example, the glue composition may be administered with a growth factor, an anti-surfactant and/or an antibiotic or other therapeutic agent, including small molecule or polypeptide drugs. Examples of growth factors that may be used include a fibroblast growth factor, a transforming growth factor-$\beta_1$, and/or a platelet-derived growth factor (PDGF), as well as functional analogs thereof. Determination of dosage ranges are well within the knowledge and/or skill of those in the art, e.g., about 1 to about 100 nM of polypeptide growth factor can be used.

Examples of antibiotics that may be used include ampicillin, sisomicin, cefotaxim, gentamycin, penicillin, nebacetin, and the like. Additionally, in some embodiments, antimicrobial agents, antiviral agents, antiseptics, bacteriocins, disinfectants, anesthetics, fungicides, anti-inflammatory agents, or other active agents or mixtures thereof may be administered with a glue composition of the present invention. Such compounds can include acetic acid, aluminum acetate, bacitracin, bacitracin zinc, benzalkonium chloride, benzethonium chloride, betadine, captan (i.e., 3α,4,7,7α-tetrahydro-2-((trichloromethyl)thio)-1H-isoindole-1,3 (2H)-dione), benzalkonium chloride, benzalkonium chloride solution, benzethonium chloride, benzoic acid, benzyl alcohol, bleomycin, calcium chloroplatinate, cephalosporin, certrimide, cetylpyridinium chloride, chlorobutanol, cloramine T, chlorhexidine phosphanilate, chlorhexidine, chlorhexidine sulfate, chloropenidine, chloroplatinatic acid, ciprofloxacin, clindamycin, clioquinol, cresol, chlorocresol, cysostaphin, dehydroacetic acid, doxorubicin, formaldehyde, gentamycin, hydroquinone, hydrogen peroxide, iodinated polyvinylidone, iodine, iodophor, imidazolidinyl urea, minocycline, mupirocin, neomycin, neomycin sulfate, nitrofurazone, non-onynol 9, o-phenylphenol, phenylmercuric additives such as phenylmercuric borate, phenylmercurie nitrate and/or phenylmercuric acetate phenol, phenylethyl alcohol, potassium benzoate, potassium sorbate, potassium permanganate, polymycin, polymycin B, polymyxin, polymyxin B sulfate, polyvinylpyrrolidone iodine, povidone iodine, 8-hydroxyquinoline, preservatives (e.g., alkyl parabens and salts thereof, such as butylparaben, ethylparaben, methylparaben, methylparaben sodium, propylparaben, propylparaben sodium, and/or pyrocatechol), quinolone thioureas, rifampin, rifamycin, resorcinol, 4-n-hexyl resoreinol, silver acetate, silver benzoate, silver carbonate, silver chloride, silver citrate, silver iodide, silver nitrate, silver oxide, silver sulfate, sodium benzoate, sodium dehydroacetate, sodium propionate, sorbic acid, sodium chloroplatinate, sodium hypochlorite, sphingolipids, sulfonamide, tetracycline, sulfadiazine salts (such as silver, sodium, and zinc), thimerosal, thymol, tiotropium bromide, zinc oxide, and the like, and any combinations thereof.

Other drug moieties that may be co-administered include, for example anti-oxidants, atropine methyl nitrate, albuterol (salbutamol) sulfate, alcetylcysteine, anticholinergics, atriopeptin, bitolterol mesylate, beta agonists, other bronchodilators, e.g., isoetharine, methylxanthines, captopril, calcitonin, cromolyn sodium, cyclosporin, ephedrine sulfate, ephedrine bitartrate, epidermal growth factor, etoposide, fluroisolide, heparin, ibuprofin, insulin, interferon, isoetharine hydrochloride, insulin, interleukin-2, isoetharine mesylate, isoproteranol hydrochloride, isoproteranol sulfate, leukotriene inhibitors, lipase inhibitors, lipocortin, lung surfactant protein, mast cell stabilizers, metaproteranol sulfate, narcotics, n-acetyl cysteine, pentamidin, non-steroidal anti-inflammatory drugs (NSAIDs), peptides, phosphodiesterase inhibitors, phospholipase inhibitors, plasma factor 8, procaterol, propranalol, pulmozyme (Genentech), P2Y2 receptor agonists, steroids, superoxide dismutase, terbutaline, terbutaline sulfate, theophylline, tissue plasminogen activator (TPA), tobermycin, tumor necrosis factor, vasopressin, and/or verapamil.

Further, the glue composition may also be administered with a nucleic acid, e.g., a nucleic acid encoding a polypeptide, antisense oligonucleotide, or interfering RNA (e.g., siRNA). Compositions of the present invention may also serve as "depot" for slow release of therapeutic moieties or other active agents at selected localized regions of damaged lung tissue.

All formulations for aerosol, trans-thoracic, instillation, intravenous and/or other administration can be formulated in dosages suitable for administration. Pharmaceutical compositions suitable for use in the present invention include glue compositions wherein the moieties and/or agents are present in an effective amount, i.e., in a diagnostically and/or pharmaceutically effective amount. A diagnostically effective amount includes a sufficient amount of a glue composition comprising an imaging moiety to allow detection of the presence of the imaging moiety, preferably at a site of sealed lung tissue, and more preferably by a non-invasive and/or in vivo imaging technique. A pharmaceutically effective amount includes a sufficient amount of a glue composition comprising an adhering moiety, cross-linkable moiety, cross-linking activating moiety and/or other agent to produce a therapeutic and/or a prophylactic benefit in at least one pulmonary condition being treated. The effective amount can be administered in a single dose or in a series of doses separated by appropriate time intervals, such as minutes, hours or days. The actual amount effective for a particular application will depend on the pulmonary condition being treated, the route of administration used, the identity of the adhering, cross-linkable, cross-linking activating and/or other moieties and/or agents to be used, and other considerations that will be appreciated by those of skill in the art. Determination of an effective amount is well within the capabilities of those skilled in the art, especially in light of the disclosures herein.

The effective amount when referring to a glue composition comprising an adhering, cross-linkable, cross-linking activating, imaging moiety and/or other moiety and/or agent will generally mean the dose ranges, modes of administration, formulations, etc., that have been recommended or approved by any of the various regulatory or advisory organizations in the medical or pharmaceutical arts (e.g., FDA, AMA) or by the manufacturer or supplier. The effective amount when referring to producing a benefit in treating a pulmonary condition, such as emphysema, will generally mean the amount that achieves clinical lung volume reduction recommended or approved by any of the various regulatory or advisory organizations in the medical or surgical arts (e.g., FDA, AMA) or by the manufacturer or supplier.

A person of ordinary skill using techniques known in the art can determine the effective amount of the adhering moiety, cross-linkable moiety, cross-linking activating moiety and/or other moiety and/or agent of the glue composition to be administered. The effective amount may depend on the moiety and/or agent to be used, and can be deduced from known data, e.g., data regarding binding constants for an adhering moiety, concentrations to achieve cross-linking for cross-linkable and cross-linking activating moieties, and sufficient imaging moiety to permit detection.

In some embodiments, dosages can be at least about 0.001 μg/kg/body weight, at least about 0.005 μg/kg/body weight, at least about 0.01 μg/kg/body weight, at least about 0.05 μg/kg/body weight, or at least about 0.1 μg/kg/body weight. In some embodiment, dosages can be less than about 0.05 mg/kg/body weight, less than about 0.1 mg/kg/body weight, less than about 0.5 mg/kg/body weight, less than about 1 mg/kg/body weight, less than about 2 mg/kg/body weight, less than about 3 mg/kg/body weight, or less than about 5 mg/kg/body weight of a composition of the invention. In some embodiment, dosages can be less than about 10 mg/kg/body weight, less than about 25 mg/kg/body weight, less than about 50 mg/kg/body weight, less than about 75 mg/kg/body weight, less than about 100 mg/kg/body weight, less than about 150 mg/kg/body weight, or less than about 200 mg/kg/body weight of a composition of the present invention.

The dosage may vary depending on the moieties used and their known biological properties. For example, it is known that fibrinogen comprises about 2 to about 4 g/L blood plasma protein and is cleaved to fibrin upon exposure to thrombin at the initiation the blood clotting cascade. In the context of reducing lung volume, formulations can be prepared containing useful concentrations of fribnogen and/or fibrin as a cross-linkable moiety and thrombin, batroxobin, a thrombin receptor agonist, and/or calcium as a cross-linking activating moiety. For example, a formulation comprising at least about 1%, at least about 2%, at least about 3%, at least about 4%, at least about 5%, at least about 8%, at least about 10%, at least about 12%, or at least about 15% fibrinogen may be used (e.g., in saline solution, for instance about 0.8%, about 0.9%, about 1%, or about 1.2% saline), and may be activated using at least about 0.5, at least about 1, at least about 5, at least about 10, or at least about 12 units of thrombin per ng of fibrinogen, and/or more than about 1 mM, more than about 1.5 mM, more than about 3 mM, more than about 5 mM, or more than about 8 mM calcium (e.g., in a $CaCl_2$ solution). Some embodiments may use a preparation of less than about 40 mM, less than about 30 mM, or less than about 20 mM calcium (e.g., in a $CaCl_2$ solution). Additionally, at least about 0.5%, at least about 1%, at least about 3%, at least about 5%, or at least about 6% of factor XIIa transglutaminanse may also be used to promote cross-linking. Formulation of fibrin-based compositions for achieving cross-linking are also known in the art, e.g., and may contain about more than about 10 mg/ml, more than about 20 mg/ml, more than about 25 mg/ml, or more than about 50 mg/ml. Fibrin-based compositions useful in the practice of this invention may also contain less than about 250 mg/ml, less than about 200 mg/ml, less than about 150 mg/ml, less than about 100 mg/ml, or less than about 50 mg/ml. See, e.g., other fibrin sealant compositions as provided in e.g., U.S. Pat. No. 5,739,288.

Further, the effective amount for use in humans can be determined from animal models, e.g., mice, rabbits, dogs, sheep, or pigs. For example, emphysema can be induced in C57BL/6 mice by administering nebulized porcine pancreatice elastase (about 30 IU/day for about 6 days), as described, for instance, in Ito, S., et al., "Tissue Heterogeneity in the Mouse Lung: Effect of Elastase Treatment" *J. Appl. Physiology* (July 2004, 97(1):204-212; available in APS, Article in PresS Mar. 12, 2004. Similarly, emphysema-like conditions may be induced in sheep exposed to papain (inhalation of about 7,000 units/week for four consecutive weeks). Emphysema can also be induced in animal models by exposure to cadmium chloride, high concentrations of oxygen, and/or cigarette smoke. Ingenito, et al., "Bronchoscopic lung volume reduction using tissue engineering principles", *American Journal of Respiratory and Critical Care Medicine*, Vol. 167 pgs. 771-778 (2003). A dose suitable for sealing damaged lung tissue in humans can be formulated based on doses found to be effective in animal models in reducing lung volume and freeing up space for expansion of remaining non-damaged or healthier tissue. Other techniques would be apparent to one of ordinary skill in the art. Further, the amount of administered glue composition comprising a cross-linkable moiety and/or coupled adhering moieties can be selected to be not so large as to generate high local hydrostatic pressures, preferably avoiding local hydrostatic pressures that exceed capillary perfusion pressure that can lead to abscess formation.

Similarly, a dose for imaging damaged lung tissue in humans can be formulated based on that used to image the lungs of a suitable animal model. Diagnostic compositions comprising an adhering moiety and an imaging moiety can be prepared using a pharmaceutically acceptable carrier and a diagnostically effective amount of the glue composition. Diagnostically effective amount required as a dose to allow imaging will depend upon the route of administration, the condition being treated, the adhering moiety being used, the imaging moiety being used, the imaging detail sought to be obtained, e.g. the extent of sealing achieved, as well as other factors that will be appreciated by those of skill in the art of medical diagnostics. One of skill in the art of medical diagnostics will readily be able to determine suitable dosages, especially in light of the disclosures provided herein.

In preferred embodiments, the dose for imaging is sufficient to detect the presence of an imaging moiety at a site of damaged (preferably sealed) lung tissue. For example, in some embodiments, radiological imaging can require that the dose provide at least about 3 μC, at least about 5 μC, or at least about 10 μC of imaging moiety. In some embodiments, radiological imaging can require that the dose provide less than about 30 μC, less than about 20 μC, or less than about 15 μC of imaging moiety. Some embodiments using magnetic resonance imaging can require a dose of at least about 0.0005 mmol/kg, at least about 0.001 mmol/kg, at least about 0.005 mmol/kg, at least about 0.01 mmol/kg, at least about 0.05 mmol/kg, at least about 0.1 mmol/kg, at least about 0.5 mmol/kg, or at least about 1 mmol/kg of imaging moiety to body weight of the subject. In some embodiments, magnetic imaging can require a dose of less than about 10 mmol/kg, less than about 8 mmol/kg, less than about 5 mmol/kg, less than about 3 mmol/kg, or less than about 2 mmol/kg of an imaging moiety to the body weight of the subject. As a further example, iodine may be used as an imaging moiety in a dose of at least about 2 mol percent, at least about 5 mol percent, at least about 7 mol percent, or at least about 8 mol percent of the administered glue composition. The iodine imaging moiety can be in a dose of less than about 20 mol percent, less than about 15 mol percent, less than about 12, or less than about 10 mole percent of the administered glue composition.

The exact dosage will be determined by the practitioner, in light of factors related to the subject in need of diagnosis and/or treatment. Factors which may be taken into account include the severity or extent of the pulmonary condition, the general health of the subject, age, weight, and diet of the subject, as well as the timing and frequency of administration, other diagnostic and/or therapeutic techniques available and/or desirable to the subject, and/or being used by the subject, as well as reaction sensitivities, allergies, tolerance and/or response to the glue composition(s) of the present invention.

Methods of Treating Pulmonary Conditions

The present invention provides methods of treating pulmonary conditions using compositions that adhere lung tissue, including damaged lung tissue. The term "pulmonary condition" as used herein refers to a non-normal condition of the lungs and/or lung tissue, for example, where there is damaged lung tissue. Examples of such pulmonary conditions include COPD, which includes emphysema, (including both heterogeneous emphysema and homogenous emphysema, preferably heterogeneous emphysema), asthma, bronchiectais, and chronic bronchitis. Pulmonary conditions can also include other chronic pulmonary disorders, sarcoidosis, pulmonary fibrosis, pneumothorax, fistulae, bronchopleural fistulae, cystic fibrosis, inflammatory states, and/or other respiratory disorders. Pulmonary conditions can also include smoking-related and/or age-related changes to the lung, as well as lung damage caused by a traumatic event, infectious agents (e.g., bacterial, viral, fungal, tuberculin and/or viral agents), exposure to toxins (e.g., chemotherapeutic agents, environmental pollutants, exhaust fumes, and/or insecticides), and/or genetic factors (e.g., alpha-1 antitrypsin deficiency and other types of genetic disorders which involve elastic and/or connective tissue degradation and/or impaired synthesis of elastic and/or connective tissues and/or impaired repair of elastic and/or connective tissues of the lungs).

One aspect of the present invention provides a method of reducing lung volume by providing a glue composition comprising a cross-linkable moiety and an adhering moiety wherein said moieties are coupled and wherein said adhering moiety adheres lung tissue; administering said glue composition to a localized region of damaged lung tissue of a subject; collapsing a first portion or all of the lung of said subject wherein said first portion comprises said localized region of damaged lung tissue; cross-linking damaged lung tissue; and re-inflating a second portion of the lung of said subject wherein said second portion does not comprise said damaged lung tissue, thereby reducing lung volume.

In some preferred embodiments, the method is performed with prior identification of the damaged lung tissue. For example, the lungs of the subject may be imaged to identify regions or sites of damaged tissue before administering a glue composition of the invention to the subject, e.g., to determine regions that may benefit from volume reduction. As used herein, the terms "regions," "sites," and "areas" are used interchangeably when referring to regions, sites and/or areas of damaged lung tissue, e.g., localize regions, sites and/or areas of damaged lung tissue selected for administration of a glue composition of the present invention. Such identification may involve any techniques known, to be developed, described herein, and/or described in U.S. nonprovisional applications entitled "Targeting Damaged Lung Tissue Using Compositions," filed Dec. 8, 2004; "Targeting Damaged Lung Tissue," filed Dec. 8, 2004; "Targeting Sites of Damaged Lung Tissue Using Composition," filed Dec. 8, 2004; "Targeting Sites of Damaged Lung Tissue," filed Dec. 8, 2004; "Imaging Damaged Lung Tissue Using Compositions," filed Dec. 8, 2004; "Imaging Damaged Lung Tissue," filed Dec. 8, 2004; "Glue Compositions for Lung Volume Reduction," filed Dec. 8, 2004; "Lung Volume Reduction Using Glue Compositions," filed Dec. 8, 2004; and "Lung Volume Reduction Using Glue Composition," filed Dec. 8, 2004, each of which is herein incorporated in its entirely that facilitate identification of regions of damaged lung tissue. Regions of damaged lung tissue include areas of the lung affected by a pulmonary condition or that are affected to a greater extent compared with other, healthier areas of the lung. In emphysema, for example, such regions can include regions featuring "blebs," that is, regions where progressive destruction of elastic tissue has caused loss of lung recoil and consequent hyper-extension.

Current techniques that may be used to identify damaged lung tissue in the present invention include radiology (e.g., chest X-rays) and CT scans. For example, review of CT scans of the chest, preferably high-resolution CT scans, can indicate localized regions of damaged lung tissue that may be selected for volume reduction.

Cross-linking of the damaged lung tissue can then bring about a reduction in lung volume, for example, by sealing and/or keeping collapsed regions of over-inflated lung tissue, preferably freeing up space for the expansion of remaining non-damaged or healthier tissue. In emphysema, for instance, regions of the lung that have lost elasticity required for exhalation can be collapsed and/or sealed by the methods described herein. Because the cross-linked tissue occupies a smaller volume than, e.g., the enlarged alveoli at sites of damaged tissue, methods of this invention can reduce lung volume overall. The present invention can thus provide a non-surgical, less-invasive and/or safer approach for achieving some of the benefits of lung volume reduction surgery.

Further, providing the glue composition to a localized region of damaged lung tissue allows for localized volume reduction, which in turn can minimize untoward side effects of lung volume reduction, such as exacerbating V/Q imbalance, changing arterial oxygenation, or triggering acute hypoxemia. Ingenito et al., (2003) Bronchoscopic Lung Volume Reduction Using tissue engineering principles, *American Journal of Respiratory and Critical Care Medicine*, Vol. 167 pgs 771-778. It is to be understood also that the methods of the present invention may be used in conjunction with a surgical procedure, such as LVRS and the use of knifeless staplers (see, e.g., Swanson et al., "No-cut thoracoscopic lung plication: A new technique for lung volume reduction surgery", *J Am Coll Surg* Vol. 185pgs 25-32 (1997)), as well as other approaches for treating pulmonary conditions, including use of coupled adhering moieties described herein.

Cross-linking of the cross-linkable moieties can be achieved by any methods known in the art and/or described herein. For example, a second composition may be administered that comprises a cross-linking activating moiety. "Cross-linking activating moiety" as used herein refers to any moiety that can bring about cross-linking between more than one cross-linkable moieties and/or that can form more than one bond with components (e.g., proteins) of lung tissue. Preferably, a cross-linking activating moiety comprises a di- or polyfunctional group. For example, where the cross-linkable moiety is at least one of a hydroxyl group, a carboxyl group, an ester group, a cyano group, a thiol group (e.g., a cysteine group), a carbonyl group, an aldehyde group, a ketone group, a primary amine group, a secondary amine group, and/or a lysine group the cross-linking activating moiety may comprise a diol, a polyol, a dicarboxylic acid (e.g., fumaric, maleic, phthalic or terephthalic acid), a polycarboxylic acid, a diester, a polyester, a diamine and/or a polyamine. The di- or polyfunctional group can form covalent linkages with more than one cross-linkable moieties, preferably between cross-linkable moieties coupled to adhering moieties binding to different sites of damaged lung tissue, e.g., at different sites within an enlarged alveolus. Linkage may include, for example, amide formation (e.g., through the condensation of an amino group with an activated ester, such as, e.g., an NHS or sulfo-NHS ester), imine formation, carbodiimide condensation, disulfide bond formation, and/or use of a specific binding pair e.g., using a biotin-avidin interaction. The cross-linking can therefore serve to seal and/or keep collapsed air spaces at sites of damaged lung tissue, e.g., in areas of over-inflated alveoli, as characteristic of certain pulmonary conditions, including emphysema.

Di- and/or polyamines that may be used in the practice of this invention include aliphatic and/or aromatic di- and/or polyamines, as well as two or more aliphatic and/or aromatic monoamines suitably linked together. For example, monomeric, di- and/or polyamines that may be used in the practice of this invention can comprise aminopyrimidine, aniline, benzidine, diaminodiphenylamine, diphenylamine, hydrazine, hydrazide, toluene-diamine, and/or triethylenediamine. Di- and/or polyamines that may be used also can comprise, for example, acetamide, acrylamide, benzamide, cyanamide, and/or urea. Di- and/or polyalcohols that may be used include aromatic and/or aliphatic alcohols, including, for example, 1,4-butanediol, phenols, polyvinyl alcohols, and/or d-sorbitol. Examples of dicarbonyls that may be used in the practice of the present invention include dicarbonyls comprising acetate, e.g., α-haloacetate derivatives, acetylacetone, diethylmalonate, ethylacetone, malonamide, malonic acid and/or malonic esters or salts thereof. Other carbonyl groups that may be used include α, β-unsaturated carbonyl groups (e.g., maleimide) and/or α-halocarbonyl groups (e.g., iodoacetamide derivatives). Di- and/or polyfunctional ketones may also be used, including, e.g., 2,5-hexanedione, and/or di- and/or polyfunctional ketones comprising two or more linked monofunctional ketones, such as cyclohexanone and/or cyclopentanone. Di- and/or polyfunctional aldehydes may also be used, see, e.g., U.S. Pat. No. 6,329,337 and/or U.S. Pat. No. 6,372,229. For example, at least one aldehyde selected from gelatin-resorcin-aldehyde, glyoxal, succinaldehyde, glutaraldehyde, malealdehyde, dextrandialdehyde, and saccharides oxidized by m-periodate may be used.

As will be appreciated by one skilled in the art, aldehydes and/or ketones described herein can exist as hydrates in aqueous solution, e.g., existing as hemi-acetals and/or hemi-ketals in aqueous solution. In preferred embodiments, such hydrates can revert back to the corresponding aldehyde and/or ketone for cross-linking. In some embodiments, hydrates of aldehydes and/or ketones and/or hydrates of other cross-linking activating moieties are themselves capable of bringing about cross-linking between more than one cross-linkable moieties and/or of forming more than one bond with components (e.g. proteins) of lung tissue.

Other cross-linking activating moieties that may (or may not) be used in the practice of the present invention include a protein or a mixture of proteins (including synthetic peptides and/or recombinant proteins), such as collagen and/or albumin and/or lipoprotein, along with other minor additives, optionally as well as hydrogel, polyglycolic acid, polylactic acid, polydioxanone, polytrimethylene carbonate, polycarprolactone, and/or glutaraldehyde, polyethylene glycol, polyethylene glycol disuccinimidoyl succinate, as well as polymerizable monomers, such as 1,1-disubstituted ethylene monomers or acetates, e.g., α-haloacetate, acrylate, acrylate glue, anhydrides cross-linked with polyols, cyano groups, e.g., cyanoacrylate, epoxy, gelatin resorcinol formaldehyde, gelatin resorcinol glutaraldehyde, hyaluronic acid cross-linked with hydrazines, photopolymerizable monomers, silicone, silicone rubber, starches, urethane, vinyl-terminated monomers, and/or any combination thereof. Other cross-linking activating moieties that may be used in the practice of the present invention include alkyl bis(2-cyanoacrylate), triallyl isocyanurate, alkylene diacrylate, alkylene dimethacrylate, and/or trimethylol propane triacrylate. Other cross-linking activating moieties that may be used in the practice of the present invention include disulfide, carbodiimide and hydrazine. Other suitable cross-linking activating moieties may be found in the art, for example, U.S. Pat. Nos. 3,940,362; 5,328, 687; 3,527,841; 3,722,599; 3,995,641; and/or 5,583,114, each incorporated herein by reference. Still another cross-linking activating moiety that may be used includes a product formed by reacting glutaraldehyde with amino acids and/or peptides, as described in U.S. Pat. No. 6,310,036. Cross-linkable and/or cross-linking activating moieties may also include suitable monomers disclosed in U.S. Publication No. 2002/0147462, such as, for instance, monomeric n-butyl-2-cyanoacrylate (Eng et al., "Successful closure of bronchopleural fistula with adhesive tissue", *Scand J Thor Cardiovasc Surg*, Vol. 24 pgs 157-59 (1990) and Inaspettato et al., "Endoscopic treatment of bronchopleural fistulas using n-butyl-2-cyanoacrylate", *Surgical Laparoscopy & Endoscopy*, Vol. 4 No. 1 pgs 62-64 (1994)).

The choice of cross-linking activating moiety can depend, at least in part, on the cross-linkable moieties used. Where the cross-linkable moiety is fibrin and/or fibrinogen, the cross-linking activating moiety may comprise a fibrin activator and/or a fibrinogen activator. For example, thrombin, a thrombin receptor agonist, batroxobin, and/or calcium can be used to initiate cross-linking of fibrinogen. It is also to be understood that any combination of cross-linking activating moieties may be used, depending on, for example, the combination of cross-linkable moieties administered. Further, some embodiments provide a glue composition comprising an adhering moiety coupled to a cross-linking activating moiety. Those of skill in the art will recognize other suitable cross-linking activating moieties that may be used in the practice of the instant invention, including, for example, any biocompatible cross-linking activating moiety that can form a biocompatible cross-linked product with a cross-linkable moiety used. In still more preferred embodiments, the cross-linkable and cross-linking activating moieties used are medically acceptable and form medically acceptable cross-links.

In some embodiments, one or more of the cross-linkable, adhering and/or cross-linking activating moieties are thermally stabilized. That is, the moiety may be modified, adapted and/or otherwise engineered to withstand heat, e.g., heat generated by a cross-linking reaction within lung tissue of a subject. For example, heat-stabilized glutaraldehyde in an aqueous carrier may be used, and in some embodiments amino acid modifications in protein adhering moieties may confer increased thermal stability.

The cross-linkable and cross-linking activating moieties can be added in appropriate ratios to facilitate cross-linking. The ratio to be used may depend on the cross-linkable and/or cross-linking activating moieties used, the rate of cross-linking desired, and/or other reaction conditions appreciated by those of skill in the art. For example, a ratio of at least about 1:1; at least about 1:2, at least about 1:5, at least about 1:10; at least about 1:15, or at least about 1:20 may be used.

It will be recognized by those of skill in the art that certain of these cross-linking activating moieties may be suitable for use alone, i.e., without a corresponding cross-linkable moiety. For example, biotin groups, amine groups, carboxylic acid groups, cyanate groups (e.g. isothiocyanate), thiol groups, disulfide groups, cyano groups (e.g., α-halocarbonyl groups, α,β-unsaturated carbonyl groups), an acetate group (e.g., α-haloacetate group), hydrazine groups, cyanoacrylate, acrylic glue, and/or silicone moieties, as well as bifunctional linkers, may be used to bring about cross-linking of damaged lung tissue without the use of a separate cross-linkable moiety. Further, various combinations of cross-linking activating moieties may be used, administered together at the same time or separately at different times of administration. For instance, a dipolyaldehyde and/or polyaldehyde may be combined with a mixture of proteins, such as albumin and/or collagen, and optionally other minor additives. Also, as mentioned above, the cross-linking activating moiety may in some embodiments be coupled to an adhering moiety, for example, to an alpha-1 antitrypsin molecule, fragment thereof, and/or derivative thereof; or to a combination of adhering moieties, including, for example, any combination of types of adhering moieties provided herein.

It is also to be understood that some embodiments would not require a cross-linking activating moiety for initiation of cross-linking. For example, if fibrin is used as the cross-linkable moiety, e.g., a fibrin monomer, such as fibrin I monomers, fibrin II monomers and/or des BB fibrin monomers, the monomers may spontaneously cross-link. For instance, fibrin I monomers may cross-link upon contacting a subject's blood, which contains thrombin and factor XII.

Various types of cross-linking reactions may be used in the practice of the present invention including, for example, free radical reactions, cross-linking by zwitterions and/or ion pairs, anions and/or cations. See e.g., U.S. Pat. Nos. 6,010, 714; 5,582,834; 5,575,997; 5,514,372; 5,514,371 and 5,328,687 to Leung et al. and U.S. Pat. No. 5,981,621. Cross-linking reactions of the present invention may also involve amide formation, imine formation, carbodiimide condensation, disulfide bond formation, and use of a specific binding pair, e.g., using a biotin-avidin interaction.

In some preferred embodiments, the method for reducing lung volume does not damage epithelial cells within lung tissues, e.g., it may not cause scar tissue formation, and/or may not cause fibroblast proliferation, and/or may not cause collagen synthesis. In some preferred embodiments, the methods cross-link and/or seal sites of damaged lung tissue within an alveolus, more preferably within an enlarged alveolus distal to a terminal bronchiole. In some preferred embodiments, the methods of the present invention do not cause occlusion of a lumen of a bronchial tube of a lung of the subject. Without being limited to a particular mechanism, methods of the present invention can reduce lung volume by keeping cross-linked and/or sealed enlarged air spaces, rather than by (mechanically) attempting to block air-flow to damaged lung tissue. That is, in preferred embodiments, cross-linking serves to keep collapsed and/or sealed blind ending sacs, rather than there being any or any substantial amount of lung tissue distal to the cross-linked sites. In yet still preferred embodiments, the lung volume reducing methods of the present invention can be carried out without the use of open surgery, e.g., thoracotomy.

In some preferred embodiments, the method for reducing lung volume can involve damage to lung tissue. For example, in some embodiments a sclerosing agent can be used as part of the administered glue composition, for instance, a sclerosing agent may be coupled to an adhering moiety of the present invention. In some embodiments, the sclerosing agent may be administered alone; or it may be administered separately at the same time as, before, or after administration of adhering, cross-linkable, and/or cross-linking activating moieties of the present invention. The sclerosing agent can serve to bring about scar tissue formation, and/or fibroblast proliferation, and/or collagen synthesis, facilitating sealing of regions of damaged lung tissue. Sclerosing agents that may be used in the present invention include Doxycycline, Bleomycin, Minocycline, Doxorubicin, Cisplatin+Cytarabine, Mitoxantrone, *Corynebacterium Parvum*, Streptokinase, Urokinase, and the like. Other agents and/or methods for damaging lung tissue may also be used in the practice of the present invention, optionally along with components of the extracellular matrix e.g., hyaluronic acid. See e.g., U.S. Publication No. 2004/0047855.

In some embodiments, cross-linking activating moieties are administered after allowing sufficient time for adhering of the administered cross-linkable moieties to lung tissue. In preferred embodiments, the adhering moiety adheres in at least about 30 seconds, at least about 1 minute, at least about 3 minutes, or at least about 5 minutes. In preferred embodiments, the adhering moiety adheres in less than about 3 hours, in less than about 2 hours, in less than about 1 hour, in less than about 45 minutes, in less than about 30 minutes, in less than about 20 minutes, or in less than about 10 minutes. Also, in some embodiments, unbound adhering moiety may be removed from the lungs, e.g., by lavage and/or washing (e.g., with saline) and/or by collapsing, before administration of cross-linking activating moiety.

Cross-linking and/or gluing may be facilitated by deflating and/or collapsing a first portion or all of the lung of the subject, preferably where the first portion comprises a selected localized region of damaged lung tissue. Such deflating and/or collapsing can be achieved by any techniques known in the art or herein disclosed. For example, the collapsing may involve the use of negative pressure from within the lung and/or positive pressure from without the lung. Also, in some embodiments, a preparation to induce and/or facilitate collapse may be used, e.g., a physiologically acceptable solution containing an anti-surfactant, such as an agent that can increase surface tension of fluids lining alveoli. For example, an anti-surfactant may be administered prior to, during and/or after administration of the composition comprising a cross-linkable moiety and/or a cross-linking activating moiety. For instance, fribrin and/or fibrinogen may be used, which can act both as an anti-surfactant as well as aiding cross-linking.

Other suitable surfactants that may be used to facilitate cross-linking and/or gluing include Triton x-100, beractant, colfosceril, and/or palmitate; anionic surfactants such as sodium tetradecyl sulfate; cationic surfactants such as tetrabutylammonium bromide and/or butyrylcholine chloride; nonionic surfactants such as polysorbate 20 (e.g., Tween 20), polysorbate 80 (e.g. Tween 80), and/or poloxamers; amphoteric and/or zwitterionic surfactants such as dodecyldimethyl (3-sulfopropyl)ammonium hydroxide, inner salt; amines, imines and/or amides, such as arginine, imidazole, povidine, tryptamine, and/or urea; alcohols such as ascorbic acid, ethylene glycol, methyl gallate, tannins and/or tannic acid; phosphines, phosphites and phosphonium salts, such as triphenylphosphine and/or triethyl phosphite; inorganic bases and/or salts, such as calcium sulfate, magnesium hydroxide, sodium silicate, and/or sodium bisulfite; sulfur compounds such as polysulfides and/or thiourea; polymeric cyclic ethers such as calixarenes, crown ethers, monensin, nonactin, and/or polymeric epoxides; cyclic and acyclic carbonates; organometallics (e.g., naphthenate and manganese acetylacetonate); phase transfer catalysts (e.g., Aliquat 336); and radical initiators and radicals (e.g., di-t-butyl peroxide and/or azobisisobutyronitrile).

Cross-linking and/or gluing may also be facilitated by filling the lung or a portion thereof with an absorbable gas, such as oxygen, e.g., to promote atelectasis. Ingenito et al., "Bronchoscope volume reduction—A safe and effective alternative to surgical therapy for emphysema," *American Journal of Respiratory and Critical Care Medicine*, Vol 164 pgs 295-301 (2001).

In some embodiments, a lavage of saline may be used to reduce the amount of surfactant naturally occurring in the lungs. Cross-linking and/or gluing may also be facilitated by use of a lavage capable of removing, e.g., any other moieties that may impede, reduce and/or otherwise interfere with adhering. For example, in some embodiments, cross-linking may be facilitated by use of an anti-secretory agent that hinders and/or prevents mucous secretion in the lung or a portion thereof. For example, the anti-secretory agent may be administered prior to, during, and/or after administration of the glue composition comprising the cross-linkable moiety and/or the cross-linking activating moiety and/or other moiety. Examples of anti-secretory agents that may be used include, for example, anticholinergic moieties, atronie, and/or atropinic moieties. Removal of mucous or excessive mucous from the lung, preferably from enlarged alveoli distal to terminal bronchioles, e.g., by washing, can also facilitate cross-linking and/or gluing and/or the adhering of an adhering moiety to lung tissue. Adhesion of a glue composition to a mucous-coated wall within a bronchus, bronchiole, or alveolus can be facilitated by virtue of adhering moieties of the present invention adhering to lung tissue and, for example, reducing and/or avoiding slippage.

In some embodiments, mechanical force may be used externally to push one area of the lung closer to another, for example, to help collapse and/or deflate an enlarged air space. A portion of a lobe of the lung may be pressed externally using, for example, a balloon, air pressure, manual pressure, and/or an instrument such as a paddle, a net, a strap that can be synched up, or magnets. In some embodiments, such pressure is applied to two or more sides of a lung lobe simultaneously. For example, endoscopes and/or magnetic probes can be used to apply local pressure (applenate) to more than one side.

In some embodiments, a first portion or all of the lung may be drawn together from the inside using, for example, a cable and hook to grab and pull tissue, for instance, towards the user. Other devices that can be used include graspers, such as an expanding grasper assembly that can be sheathed; and/or anchors that can be left behind, for example, by being uncoupled from a cable or wire after lung tissue has been drawn together. In some embodiments, magnetic probes can be placed at different locations within the lung where the probes attract one another, thereby attracting one region of the lung to the other, e.g., one bronchi to another. Additionally, mechanical force may be used to change the shape of such devices after insertion, such as by using a core wire or activating a NiTi device after placement. In still other embodiments, the lungs or a first portion thereof are deflated transthoracically. Other methods and/or devices known in the art to facilitate lung deflation and/or collapse may also be employed, e.g. see U.S. Publication No. 2003/0070682.

Such deflating and/or collapsing is preferably carried out after allowing sufficient time for distribution of the administered glue composition to damaged lung tissue. In some embodiments, for example, deflating and/or collapsing is carried out approximately 2 to approximately 3 minutes after administration. Also, the lung, or a first portion thereof, is preferably allowed to remain in a collapsed and/or deflated state for a time sufficient to permit cross-linking and/or gluing to take place, sealing segments of the lung to which the glue composition has been administered. Depending on the glue composition used, e.g., the adhering moieties used, the lung or a first portion thereof can be kept deflated and/or collapsed for at least approximately 3 days, at least approximately 2 days (48 hours), at least approximately 24 hours, at least approximately 12 hours, at least approximately 5 hours, at least approximately 1 hour, at least approximately 45 minutes, at least approximately 20 minutes, at least approximately 10 minutes, at least approximately 5 minutes, at least approximately 2 minutes, at least approximately 1 minute, at least approximately 30 seconds, or at least approximately 15 seconds. In some embodiments, the lung or a first portion thereof can be kept deflated and/or collapsed for less than about 30 minutes, less than about 20 minutes, less than about 10 minutes, or less than about 8 minutes.

In some embodiments, a catalytic amount of a rate modifier may be added to modify the rate of the cross-linking and/or gluing reaction. For example, various set or cure times may be used, where the cross-linking reaction occurs in at least about 20 seconds, at least about 30 seconds, at least about 1 minute, at least about 90 seconds, at least about 2 minutes, at least about 150 seconds, at least about 3 minutes, at least about 4 minutes, at least about 5 minutes, at least about 6 minutes, at least about 10 minutes, or at least about 15 minutes. The cross-linking reaction may occur in less than about 20 minutes, in less than about 25 minutes, in less than about 30 minutes, in less than about 1 hour, in less than about 2 hours, or in less than about 3 hours. Cure times may be tailored by use of various techniques known in the art, for example, by using buffers having different pH values.

A second portion of the lung can then be re-inflated, where the second portion comprises part, but preferably not all, of the first portion or all of the lung that was deflated and/or collapsed. In preferred embodiments, this second portion does not comprise at least some damaged lung tissue, which remains collapsed and/or sealed by virtue of the cross-linking and/or gluing. The cross-linking and/or gluing preferably forms a stable mesh that keeps the collapsed region from re-inflating. In more preferred embodiments, the majority of damaged lung tissue remains cross-linked and/or glued (and thereby collapsed), while the majority of non-damaged lung tissue is left in a functional condition. For example, at least about 60%, at least about 80%, and most preferably at least about 90% of damaged lung tissue is cross-linked and/or glued; while less than about 40%, less than about 20%, and most preferably less than about 10% of non-damaged lung tissue remains not cross-linked and/or not glued. Reduction in overall lung volume improves mechanical function, e.g., mechanical functioning of healthier and/or more elastic tissue.

In preferred embodiments, cross-linking and/or gluing results in at least about a 0.5% overall lung volume reduction, at least about a 1% overall lung volume reduction, at least about a 1.5% overall lung volume reduction, at least about a 2% overall lung volume reduction, at least about a 3% overall lung volume reduction, at least about a 4% overall lung volume reduction, at least about a 5% overall lung volume reduction, or at least about a 10% overall lung volume reduction. In preferred embodiments, cross-linking and/or gluing results in less than about a 40%, less than about a 35%, less than about a 30%, less than about a 25%, less than about a 20%, or less than about a 15% overall lung volume reduction. Such reduction may be achieved upon a single or multiple administrations of compositions of the present invention. A reduction of about 2% to about 3% overall lung volume reduction can be expected to produce a beneficial effect in a subject receiving such treatment, e.g., at least to a similar extent as that produced in LVRS.

Also in preferred embodiments, the cross-linking and/or gluing is permanent, or at least semi-permanent, for a period of time between successive treatments as described herein, e.g., resisting biodegradation (e.g., hydrolysis) for the period of time between administrations of a glue composition of the present invention. In certain embodiments, at least about 70%, at least about 80%, at least about 90%, or at least about 98% of the cross-links and/or glue remain intact for a period of time. In some preferred embodiments, the period is at least about one month, at least about 2 months, at least about 3 months, at least about 6 months, at least about a year, at least about 2 years, at least about 3 years, at least about 5 years, or at least about 10 years. In some preferred embodiments, the period is less than about 50 years, less than about 30 years, less than about 20 years, or less than about 15 years. In most preferred embodiments, the cross-linking and/or gluing keeps some damaged lung tissue collapsed and/or sealed for the remainder of the life of the subject, for example, resisting biodegradation indefinitely.

One of skill in the art will recognize that the permanence and/or biodegradability of the cross-links and/or glue can depend on the cross-linkable moiety, the cross-linking activating moiety, and/or the conditions of cross-linking and/or other agents and/or moieties used, and can be controlled accordingly, e.g., by techniques known the art and/or disclosed herein.

In preferred embodiments, some or all of the cross-links and/or glue are strong enough to withstand mechanical pressures experienced within the lung. For example, the strain range corresponding to functional residual capacity during normal breathing does not result in breakage of at least about 30%, at least about 40%, at least about 50%, at least about 60%, at least about 70%, at least about 80%, at least about 90%, or at least about 95% of the cross-links and/or glue in some preferred embodiments.

In some preferred embodiments, the cross-links and/or glue exhibit a tear strength of at least about 50 g/sq. cm, at least about 100 g/sq. cm, at least about 200 g/sq. cm, or at least about 300 g/sq. cm. In some preferred embodiments, the cross-links and/or glue exhibit a tear strength of 5,000 g/sq. cm, less than about 3,000 g/sq. cm, less than about 1500 g/sq. cm, less than about 1300 g/sq. cm, less than about 1200/g/sq. cm, less than about 1000 g/sq. cm, less than about 800 g/sq. cm, less than about 600 g/sq. cm, or less than about 400 g/sq. cm.

Similarly, in preferred embodiments, the binding interaction between an adhering moiety and lung tissue is permanent, or at least semi-permanent, for a period of time between successive treatments as described herein, e.g., binding irreversibly, substantially irreversibly, or at least with a high binding constant, e.g., to resist dissociation for the period of time between administrations of a glue composition of the present invention. For example, an alpha-1 antitrypsin moiety may form a pseudo-irreversible equimolar complex with neutrophil elastase in some embodiments. See, e.g., Sifers et al., "Genetic Control of Human Alpha-1 Antitrypsin", *Mol. Biol. Med*, Vol. 6 pgs. 127-135 (1989). Without being limited to a particular theory or mode of action, the alpha-1 antitrypsin moiety may form an acyl-enzyme complex with an elastase component of lung tissue. In some embodiments, binding can be further enhanced by genetic modification or by shuffling of known binding domains. As another example, a serpin moiety may react with its corresponding protease to form a sodium dodecyl sulfate(SDS)-stable equimolar complex. Without being limited to a particular theory or mode of action, the complex between a serpin and its corresponding protease may involve a covalent ester bond linkage, where an active site Serine residue of the protease binds a C-terminal residue of a cleaved form of the serpin to form an acyl-enzyme complex. See, e.g., U.S. Publication No. 2003/0216321. As yet another example, a monocyte elastase inhibitor moiety can form a covalent complex and/or an essentially irreversible complex with elastase. See, e.g., International Publication WO 96/10418 and U.S. Pat. No. 5,827,672.

In certain embodiments, at least about 70%, at least about 80%, at least about 90%, or at least about 98% of the adhering moieties remain bound to lung tissue for a period of time. In some preferred embodiments, the period is at least about one month, at least about 2 months, at least about 3 months, at least about 6 months, at least about a year, at least about 2 years, at least about 3 years, at least about 5 years, or at least about 10 years. In some preferred embodiments, the period is less than about 50 years, less than about 30 years, less than about 20 years, or less than about 15 years. In most preferred embodiments, the binding keeps some damaged lung tissue collapsed and/or sealed for the remainder of the life of the subject, for example, resisting dissociation indefinitely.

FIG. 1*a* illustrates one embodiment of a method to reduce lung volume using a glue composition comprising a cross-linkable moiety coupled to an adhering moiety that adheres to lung tissue. This figure provides an overview only, and is in no way intended to be limiting with respect to the present invention. For example, those skilled in the art will readily appreciate variations and modifications of the scheme illustrated. FIG. 1*a* schematically illustrates a bronchoscope placed in a bronchus from which a catheter extends to a segmental and subsegmental bronchus. The catheter features a distended balloon-like structure near its distal tip. The balloon-like structure anchors the catheter within the subsegmental bronchus, positioning it for delivery of a glue composition of the present invention in aerosol and/or non-aerosol form to a selected localized region of damaged lung tissue.

FIG. 1*b* schematically illustrates a terminal bronchiole, terminating in the airspace of an alveolus. The figure also illustrates a component of lung tissue found within the walls of the air space and/or within the epithelial lining fluid. As mentioned above, the airspace may be over-inflated and/or enlarged in certain pulmonary conditions, such as emphysema.

A glue composition of the invention is administered, where the glue composition comprises a cross-linkable moiety (X) coupled to an adhering moiety that can adhere to lung tissue, such as a component of lung tissue. FIG. 1*b* illustrates how different adhering moieties adhere to lung tissue components at various sites within the air space.

Following collapse and cross-linking, the cross-linkable moieties become cross-linked, for example, via a cross-linking activating moiety. The cross-linking activating moiety may comprise a di-functional group, depicted in the figure as —Y—R—Y—, where Y represents a group capable of coupling to the cross-linkable moieties (X), e.g., to form covalent linkages between two cross-linkable moieties, and R represents a linking moiety between the Y groups, for example, but not limited to, an aliphatic chain. The cross-linking activating moiety couples the cross-linkable moieties that are themselves coupled to adhering moieties bound to lung tissue components found at various sites within the air space. FIG. 1*b* illustrates how cross-linking can keep the walls of the air space closer together even after re-inflation of the lung, thereby reducing overall lung volume.

The methods of reducing lung volume described herein find use in the treatment of a number of pulmonary conditions in animal subjects. The term "animal subject" as used herein includes humans as well as other mammals. The term "treating" as used herein includes achieving a therapeutic benefit and/or a prophylactic benefit. By therapeutic benefit is meant eradication or amelioration of the underlying pulmonary condition being treated. For example, in an emphysematous patient, therapeutic benefit includes eradication or amelioration of the underlying emphysema, including improved lung function, exercise capacity, quality of life, and reduced hospitalization. Also, a therapeutic benefit is achieved with the eradication or amelioration of one or more of the physiological symptoms associated with the underlying pulmonary condition such that an improvement is observed in the subject, notwithstanding the fact that the subject may still be afflicted with the pulmonary condition. For example, with respect to emphysema, administration of compositions of the invention can provide therapeutic benefit not only when areas lacking elasticity are collapsed, but also when an improvement is observed in the subject with respect to other disorders that accompany emphysema like chronic pulmonary infection. For example, addition of adhering moieties comprising protease inhibitors may ameliorate emphysema by reducing protease activity, e.g., as described in the art. For prophylactic benefit, a glue composition of the present invention may be administered to a subject at risk of developing a pulmonary condition, for example, emphysema, or to a subject reporting one or more of the physiological symptoms of such a condition, even though a diagnosis may not have been made.

Another aspect of the present invention provides a method of reducing lung volume by providing a glue composition comprising a first adhering moiety and a second adhering moiety wherein said adhering moieties are coupled and wherein said adhering moieties adhere lung tissue; administering said glue composition to a localized region of damaged lung tissue of a subject; collapsing a first portion or all of the lung of said subject wherein said first portion comprises said localized region of damaged lung tissue; allowing said adhering moieties to adhere different sites of lung tissue, and re-inflating a second portion of the lung of said subject wherein said second portion does not comprise said damaged lung tissue, thereby reducing lung volume.

In preferred embodiments, the different sites comprise different sites within an enlarged air space, e.g., within alveolar walls of an over-inflated alveolus distal to a terminal bronchiole, as characteristic of some pulmonary conditions, including emphysema. For example, the first adhering moiety can adhere to a first component of lung tissue and the second adhering moiety can adhere to a second component of lung tissue, where the first and second components occur at different sites. As the coupled adhering moieties bind to different sites within an air space, following deflation and/or collapse, the coupled adhering moieties can act to keep different sites closer together, thereby keeping the air space in a collapsed and/or sealed state. Also regions of damaged lung tissue can be selectively collapsed and/or sealed by administering a glue composition of the present invention to a selected localized region of damaged lung tissue, preferably freeing up space for the expansion of remaining non-damaged or healthier tissue.

In some preferred embodiments, the method is performed with prior identification of the damaged lung tissue. For example, the lungs of the subject may be imaged to identify regions or sites of damaged tissue before administering a glue composition of the invention to the subject. Such identification may involve any techniques known in the art, to be developed, described herein, and/or described in U.S. non-provisional applications entitled "Targeting Damaged Lung Tissue Using Compositions," filed Dec. 8, 2004; "Targeting Damaged Lung Tissue," filed Dec. 8, 2004; "Targeting Sites of Damaged Lung Tissue Using Composition," filed Dec. 8, 2004; "Targeting Sites of Damaged Lung Tissue," filed Dec. 8, 2004; "Imaging Damaged Lung Tissue Using Compositions," filed Dec. 8, 2004; "Imaging Damaged Lung Tissue," filed Dec. 8, 2004; "Glue Compositions for Lung Volume Reduction," filed Dec. 8, 2004; "Lung Volume Reduction Using Glue Compositions," filed Dec. 8, 2004; and "Lung Volume Reduction Using Glue Composition," filed Dec. 8, 2004, each of which is herein incorporated in its entirely that facilitate identification of regions of damaged lung tissue. Regions of damaged lung tissue include areas of the lung affected by a pulmonary condition or that are affected to a greater extent compared with other, healthier areas of the lung. In emphysema, for example, such regions can include regions featuring "blebs," that is, regions where progressive destruction of elastic tissue has caused loss of lung recoil and consequent hyper-extension.

Current techniques that may be used to identify damaged lung tissue in the present invention include radiology (e.g., chest X-rays) and CT scans. For example, review of CT scans of the chest, preferably high-resolution CT scans, can indicate localized regions of damaged lung tissue that may be selected for volume reduction.

Because the collapsed tissue occupies a smaller volume than the enlarged alveoli at sites of damaged tissue, methods of this invention can reduce lung volume overall. The present invention can thus provide a non-surgical, less-invasive and/or safer approach for achieving at least some of the benefits of lung volume reduction surgery. Further, providing the glue composition to a localized region of damaged lung tissue allows localized volume reduction, which in turn minimizes untoward side effects, such as exacerbating V/Q imbalance, changing arterial oxygenation, or triggering acute hypoxemia. Ingenito et al., "Bronchoiscopic Lung Volume Reduction Using tissue engineering principles", *American Journal of Respiratory and Critical Care Medicine*, Vol. 167 pgs. 771-778 (2002). It is to be understood also that the methods of the present invention may be used in conjunction with a surgical procedure, such as LVRS, as well as other approaches for treating pulmonary conditions, including cross-linking and/or gluing methods described herein, and/or other methods described in any of the applications entitled "Targeting Damaged Lung Tissue Using Compositions," filed Dec. 8, 2004; "Targeting Damaged Lung Tissue," filed Dec. 8, 2004; "Targeting Sites of Damaged Lung Tissue Using Composition," filed Dec. 8, 2004; "Targeting Sites of Damaged Lung Tissue," filed Dec. 8, 2004; "Imaging Damaged Lung Tissue Using Compositions," filed Dec. 8, 2004; "Imaging Damaged Lung Tissue," filed Dec. 8, 2004; "Glue Compositions for Lung Volume Reduction," filed Dec. 8, 2004; "Lung Volume Reduction Using Glue Compositions," filed Dec. 8, 2004; and "Lung Volume Reduction Using Glue Composition," filed Dec. 8, 2004, each of which is herein incorporated in its entirely.

In some preferred embodiments, the method for reducing lung volume does not damage epithelial cells within lung tissues, e.g., it may not cause scar tissue formation, and/or may not cause fibroblast proliferation, and/or may not cause collagen synthesis. In some preferred embodiments, the methods cross-link and/or seal sites of damaged lung tissue within an alveolus, more preferably within an enlarged alveolus distal to a terminal bronchiole. In some preferred embodiments, the methods of the present invention do not cause occlusion of a lumen of a bronchial tube of a lung of the subject. Without being limited to a particular mechanism, methods of the present invention can reduce lung volume by sealing enlarged air spaces, rather than by (mechanically) attempting to block air-flow to damaged lung tissue. That is, in preferred embodiments, administering a glue composition to a localized region of damaged lung tissue serves to seal and/or keep collapsed blind ending sacs, rather than there being any or any substantial amount of lung tissue distal to the collapsed region. In yet still preferred embodiments, the lung volume reducing methods of the present invention can be carried out without the use of open surgery, e.g., thoracotomy.

In some preferred embodiments, the method for reducing lung volume can involve damage to lung tissue. For example, in some embodiments a sclerosing agent can be used as part of the administered glue composition, for instance, a sclerosing agent may be coupled to an adhering moiety of the present invention. In some embodiments, the sclerosing agent may be administered alone; or it may be administered separately at the same time as, before, or after administration of adhering moieties of the present invention. The sclerosing agent can serve to bring about scar tissue formation, and/or fibroblast proliferation, and/or collagen synthesis, facilitating sealing of regions of damaged lung tissue. Sclerosing agents that may be used in the present invention include Doxycycline, Bleomycin, Minocycline, Doxorubicin, Cisplatin+Cytarabine, Mitoxantrone, *Corynebacterium Parvum*, Streptokinase, Urokinase, and the like. Other agents and/or methods for damaging lung tissue may also be used in the practice of the present invention, optionally along with components of the extracellular matrix, e.g., hyaluronic acid. See e.g., U.S. Publication No. 2004/0047855.

Collapse of lung tissue, e.g., collapse of an enlarged air spaces within which a glue composition of the present invention adheres, may involve deflating and/or collapsing a first portion or all of the lung of the subject, preferably where the first portion comprises the selected localized region of damaged lung tissue. Such collapsing can be achieved by any techniques known in the art or herein disclosed. For example, the deflating and/or collapsing may involve the use of negative pressure from within the lung and/or positive pressure from without the lung. Also, in some embodiments, a preparation to induce and/or facilitate deflation and/or collapse may be used, e.g., a physiologically acceptable solution containing an anti-surfactant, such as an agent that can increase surface tension of fluids lining alveoli. For example, an anti-surfactant may be administered prior to, during and/or after administration of the composition comprising coupled adhering moieties. For instance, fribrin and/or fibrinogen may be used. In some embodiments, a lavage of saline may be used to reduce the amount of surfactant naturally occurring in the lungs. Other suitable surfactants that may be used to facilitate collapse and/or deflation include Triton x-100, beractant, colfosceril, and/or palmitate; anionic surfactants such as sodium tetradecyl sulfate; cationic surfactants such as tetrabutylammonium bromide and/or butyrylcholine chloride; nonionic surfactants such as polysorbate 2 (e.g., Tween 20), polysorbate 80 (e.g. Tween 80), and/or poloxamers; amphoteric and/or zwitterionic surfactants such as dodecyldimethyl(3-sulfopropyl)ammonium hydroxide, inner salt; amines, imines and/or amides, such as arginine, imidazole, povidine, tryptamine, and/or urea; alcohols such as ascorbic acid, ethylene glycol, methyl gallate, tannins and/or tannic acid; phosphines, phosphites and phosphonium salts, such as triphenylphosphine and/or triethyl phosphite; inorganic bases and/or salts, such as calcium sulfate, magnesium hydroxide, sodium silicate, and/or sodium bisulfite; sulfinur compounds such as polysulfides and/or thiourea; polymeric cyclic ethers such as calixarenes, crown ethers, monensin, nonactin, and/or polymeric epoxides; cyclic and acyclic carbonates; organometallics (e.g., naphthenate and manganese acetylacetonate); phase transfer catalysts (e.g., Aliquat 336); and radical initiators and radicals (e.g., di-t-butyl peroxide and/or azobisisobutyronitrile).

Deflation and/or collapse may also be facilitated by use of a lavage capable of removing any other moieties that may impede, reduce and/or otherwise interfere with adhering. For example, in some embodiments, cross-linking may be facilitated by use of an anti-secretory agent that hinders and/or prevents mucous secretion in the lung or a portion thereof. For example, the anti-secretory agent may be administered prior to, during, and/or after administration of the glue composition comprising coupled adhering moieties. Examples of anti-secretory agents that may be used include, for example, anti-cholinergic moieties, atronie, and/or atropinic moieties. Removal of mucous or excessive mucous from the lung, preferably from enlarged alveoli distal to terminal bronchioles, e.g., by washing, can also facilitate binding of the coupled adhering moieties to lung tissue. Adhesion of a composition of the present invention to a mucous-coated wall within a bronchus, bronchiole, or alveolus can be facilitated by virtue of adhering moieties of the present invention adhering components of lung tissue and, e.g., reducing and/or avoiding slippage.

In some embodiments, mechanical force may be used externally to push one area of the lung closer to another, for example, to help collapse an enlarged air space: A portion of a lobe of the lung may be pressed externally using, for example, a balloon, air pressure, manual pressure, and/or an instrument such as a paddle, a net, a strap that can be synched up, or magnets. In some embodiments, such pressure is applied to two or more sides of a lung lobe simultaneously. For example, endoscopes and/or magnetic probes can be used to apply local pressure (applenate) to more than one side.

In some embodiments, a first portion or all of the lung may be drawn together from the inside using, for example, a cable and hook to grab and pull tissue, for instance, towards the user. Other devices that can be used include graspers, such as an expanding grasper assembly that can be sheathed; and/or anchors that can be left behind, for example, by being uncoupled from a cable or wire after lung tissue has been drawn together. In some embodiments, magnetic probes can be placed at different locations within the lung where the probes attract one another, thereby attracting one region of the lung to the other, e.g., one bronchi to another. Additionally, mechanical force may be used to change the shape of devices after insertion, such as by using a core wire or activating a NiTi device after placement. In still other embodiments, the lungs or a first portion thereof are deflated trans-thoracically. Other methods and/or devices known in the art to facilitate lung collapse may also be employed, e.g. see U.S. Publication No. 2003/0070682.

Such deflation and/or collapsing is preferably carried out after allowing sufficient time for distribution of the administered glue composition to a selected localized region of damaged lung tissue. In some embodiments, for example, deflation and/or collapse is carried out approximately 2 to approximately 3 minutes after administration of a glue composition of the present invention. Also, the lung, or a first portion thereof, is preferably allowed to remain in a deflated and/or collapsed state for a time sufficient to permit adhering of more than one of the coupled adhering moieties to lung tissue components at different sites of lung tissue in localized regions to which the glue composition has been administered. Depending on the glue composition used, e.g., the adhering moieties used, the lung or a first portion thereof can be kept deflated and/or collapsed for at least approximately 3 days, at least approximately 2 days (48 hours), at least approximately 24 hours, at least approximately 12 hours, at least approximately 5 hours, at least approximately 1 hour, at least approximately 45 minutes, at least approximately 20 minutes, at least approximately 10 minutes, at least approximately 5 minutes, at least approximately 2 minutes, at least approximately 1 minute, at least approximately 30 seconds, or at least approximately 15 seconds. In some embodiments, the lung or a first portion thereof can be kept deflated and/or collapsed for less than about 30 minutes, less than about 20 minutes, less than about 10 minutes, or less than about 8 minutes.

A second portion of the lung can then be re-inflated, where the second portion comprises part, but preferably not all, of the first portion or all of the lung that was deflated and/or collapsed. In preferred embodiments, this second portion does not comprise at least some damaged lung tissue, which remains collapsed and/or sealed by virtue of coupled adhering moieties bound to different sites of damaged lung tissue. The adhering preferably keeps the collapsed region from re-inflating. In more preferred embodiments, the majority of damaged lung tissue remains collapsed and/or sealed, while the majority of non-damaged lung tissue is left in a functional condition. For example, at least about 60%, at least about 80%, and most preferably at least about 90% of damaged lung tissues is collapsed; while less than about 40%, less than about 20%, and most preferably less than about 10% of non-damaged lung tissue is not and/or re-inflates. Reduction in overall lung volume improves mechanical function, e.g., mechanical functioning of healthier and/or more elastic tissue.

In preferred embodiments, binding of coupled adhering moieties results in at least about a 0.5% overall lung volume reduction, at least about a 1% overall lung volume reduction, at least about a 1.5% overall lung volume reduction, at least about a 2% overall lung volume reduction, at least about a 3% overall lung volume reduction, at least about a 4% overall lung volume reduction, at least about a 5% overall lung volume reduction, at least about a 10% overall lung volume reduction. In preferred embodiments binding of coupled adhering moieties results in less than about a 40%, less than about a 35%, less than about a 30%, less than about a 25%, less than about a 20%, or less than about a 15% overall lung volume reduction. Such reduction may be achieved upon a single or multiple administrations of glue compositions of the present invention. A reduction of about 2% to about 3% overall lung volume reduction can be expected to produce a beneficial effect in a subject receiving such treatment, e.g., at least to a similar extent as that produced in LVRS.

Also in preferred embodiments, the coupling between adhering moieties is permanent or at least semi-permanent for a period of time between successive treatments as described herein, e.g., resisting biodegradation (e.g., hydrolysis) for the period of time between administrations of a glue composition of the present invention. In certain embodiments, at least about 70%, at least about 80%, at least about 90%, or at least about 98% of the coupling between adhering moieties remains intact for a period of time. In some preferred embodiments, the period is at least about one month, at least about 2 months, at least about 3 months, at least about 6 months, at least about a year, at least about 2 years, at least about 3 years, at least about 5 years, or at least about 10 years. In some preferred embodiments, the period is less than about 50 years, less than about 30 years, less than about 20 years, or less than about 15 years. In most preferred embodiments, the coupled adhering moieties keep some damaged lung tissue collapsed and/or sealed for the remainder of the life of the subject, for example, resisting biodegradation indefinitely. One of skill in the art will recognize that the permanence and/or biodegradability of the coupling between adhering moieties can depend on the coupling technique chosen and/or the coupling moiety used.

In preferred embodiments, some or all of the coupling moieties are strong enough to withstand mechanical pressures experienced within the lung. For example, the strain range corresponding to functional residual capacity during normal breathing does not result in breakage of at least about 30%, at least about 40%, at least about 50%, at least about 60%, at least about 70%, at least about 80%, at least about 90%, or at least about 95% of the coupling moieties in some preferred embodiments.

In some preferred embodiments, the coupling moieties exhibit a tear strength of at least about 50 g/sq. cm, at least about 100 g/sq. cm, at least about 200 g/sq. cm, or at least about 300 g/sq. cm. In some preferred embodiments, the coupling moieties exhibit a tear strength of less than about 5,000 g/sq. cm, less than about 3,000 g/sq. cm, less than about 1500 g/sq. cm, less than about 1300 g/sq/cm, less than about 1200 g/sq. cm, less than about 1000 g/sq. cm, less than about 800 g/sq. cm, less than about 600 g/sq. cm, or less than about 400 g/sq. cm.

Similarly, in preferred embodiments, the binding between adhering moieties and lung tissue is permanent or at least semi-permanent for a period of time between successive treatments as described herein, e.g., binding irreversibly, substantially irreversibly, or at least with a high binding constant to resist dissociation for the period of time between administrations of a glue composition of the present invention. For example, an alpha-1 antitrypsin moiety may form a pseudo-irreversible equimolar complex with neutrophil elastase in some embodiments. See, e.g., Sifers et al., "Genetic Control of Human Alpha-1 Antitrypsin", *Mol. Biol. Med.*, Vol. 6 pgs. 127-135 (1989). Without being limited to a particular theory or mode of action, the alpha-1 antitrypsin moiety may form an acyl-enzyme complex with an elastase component of lung tissue. In some embodiments, binding can be further enhanced by genetic modification or by shuffling of known binding domains. As another example, a serpin moiety may react with its corresponding protease to form a sodium dodecyl sulfate(SDS)-stable equimolar complex. Without being limited to a particular theory or mode of action, the complex between a serpin and its corresponding protease may involve a covalent ester bond linkage, where an active site Serine residue of the protease binds a C-terminal residue of a cleaved form of the serpin to form an acyl-enzyme complex. See, e.g., U.S. Publication No. 2003/0216321. As yet another example, a monocyte elastase inhibitor moiety can form a covalent complex and/or an essentially irreversible complex with elastase. See, e.g., International Publication WO 96/10418 and U.S. Pat. No. 5,827,672.

In certain embodiments, at least about 70%, at least about 80%, at least about 90%, or at least about 98% of the adhering moieties remain bound to lung tissue for a period of time. In some preferred embodiments, the period is at least about one month, at least about 2 months, at least about 3 months, at least about 6 months, at least about a year, at least about 2 years, at least about 3 years, at least about 5 years, or at least about 10 years. In some preferred embodiments, the period is less than about 50 years, less than about 30 years, less than about 20 years, or less than about 15 years. In most preferred embodiments, the adhering keeps some damaged lung tissue collapsed and/or sealed for the remainder of the life of the subject, for example, resisting dissociation indefinitely.

Figure 2A:
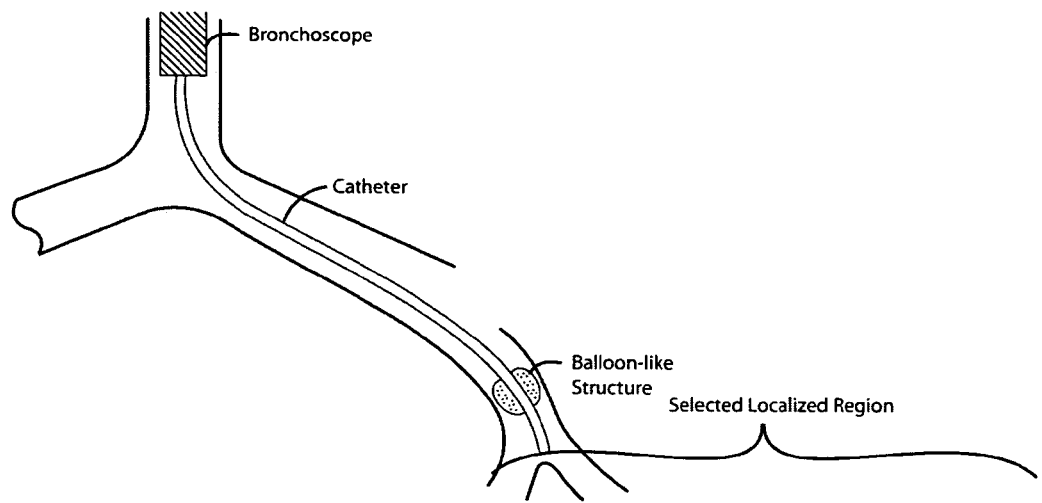
FIG. 2a schematically illustrates a bronchoscope placed in a bronchus from which a catheter extends to a segmental and subsegmental bronchus.

FIG. 2 illustrates one embodiment of a method to reduce lung volume using a glue composition comprising coupled adhering moieties. This figure provides an overview only, and is in no way intended to be limiting with respect to the present invention. For example, those skilled in the art will readily appreciate variations and modifications of the scheme illustrated. FIG. 2a schematically illustrates a bronchoscope placed in a bronchus from which a catheter extends to a segmental and subsegmental bronchus. The catheter features a distended balloon-like structure near its distal tip. The balloon-like structure anchors the catheter within the subsegmental bronchus, positioning it for delivery of a glue composition of the present invention in aerosol and/or non-aerosol form to a selected localized region of damaged lung tissue.

Figure 2B:
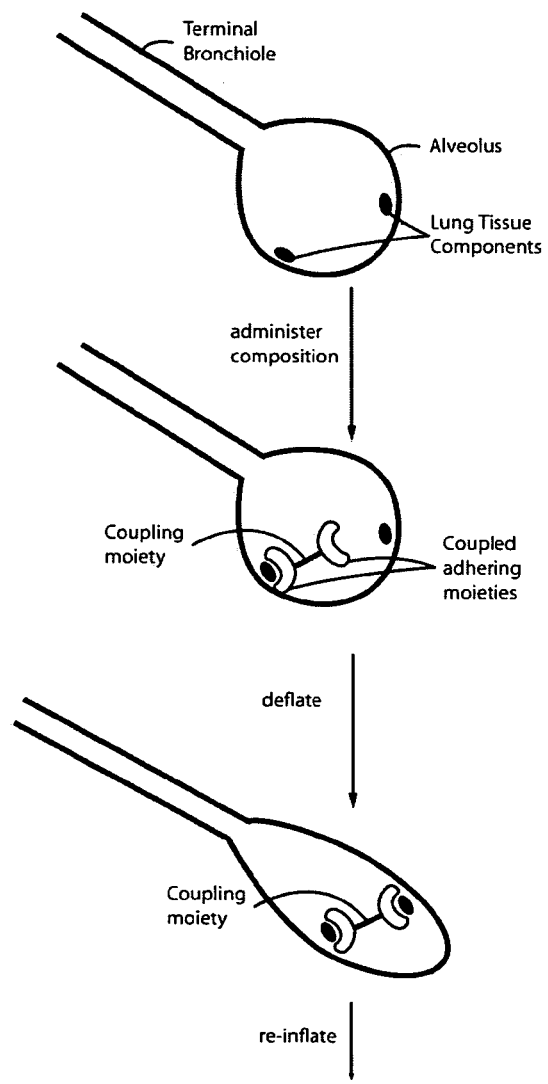
FIG. 2b schematically illustrates a terminal bronchiole, terminating in the airspace of an alveolus.

FIG. 2b schematically illustrates a terminal bronchiole, terminating in the airspace of an alveolus. The figure also illustrates lung tissue components found within the walls of the airspace and/or within the epithelial lining fluid. As mentioned above, the air space may be over-inflated and/or enlarged in certain pulmonary conditions, such as emphysema.

A glue composition of the invention is administered, where the glue composition comprises adhering moieties that are coupled, for example, via a coupling moiety. FIG. 2b illustrates how, following administration, one of the adhering moieties can adhere to a lung tissue component within the air space.

FIG. 2b also illustrates how the two adhering moieties can adhere to lung tissue components at two different sites within the air space. Following deflation, the walls of the alveolus are brought into closer proximity, allowing the second adhering moiety to adhere to a lung tissue component at a different site within the air space. The binding of coupled adhering moieties to hitherto further-apart sites of lung tissue serves to help keep the walls of the air space closer together. A previously enlarged and/or distended alveolus may thus be kept in a collapsed and/or sealed state after re-inflation, thereby reducing overall lung volume.

Glue compositions of the present invention may also comprise an imaging moiety, for example, an imaging moiety coupled to an adhering moiety, a cross-linkable moiety, a cross-linking moiety and/or a sclerosing agent used. An imaging moiety may assist in non-intrusive visualization and/or monitoring of the collapsed and/or sealed lung tissue. For example, imaging moieties can afford detection of sealed damaged lung tissue and preferably facilitate monitoring of the presence, position, extent, and/or degradation of the cross-links, coupling moieties and/or glue, and/or dissociation of the adhering moiety.

The imaging moiety may be imaged by any methods known in the art and/or described herein. For example, imaging may be carried out via traditional radiological techniques, including, for example the use of an X-ray, computer tomography (CT), and/or the use of more advanced techniques such as a positron emission tomography (PET) scan, nuclear scans, and/or scintigraphy, as well as magnetic resonance imaging (MRI), functional magnetic resonance imaging (FMRI), magnetoencephalography (MEG), and single photon emission computerized tomography (SPECT). Such imaging techniques can be used to detect localized imaging moieties in vitro or in vivo, preferably in vivo. High resolution scans, e.g., a high resolution CT scan, are preferable. In more preferred embodiments, such imaging produces a detailed map of the lungs, showing sites of glued and/or sealed tissue and/or the extent of collapse, e.g., by the concentration of imaging moieties at localized sites within the lungs to which the glue composition was administered.

The method of detection used may depend on the imaging moiety administered. For example, ultrasound imaging can be used to detect an echogenic imaging moiety and/or an imaging moiety capable of generating an echogenic signal and/or other ultrasound imaging moieties. X-ray can be used to detect a heavy atom imaging moiety (e.g., having atomic weight of about 38 or above). Light imaging can be used to detect an imaging moiety capable of scattering and/or absorbing and/or emitting light. MR imaging can be used to detect an imaging moiety comprising a non-zero nuclear spin isotope (such as F-19) and/or an imaging moiety having unpaired electron spins. PET, scintigraphy, and/or SPECT can be used to detect a radionuclide imaging moiety.

For example, in some embodiments, an imaging moiety comprising a radioactive gamma emitter can be used, and can be detected via a gamma camera, scintillation counter, and/or other device capable of detecting gamma radiation. Radiation imaging cameras can use a conversion medium to absorb high-energy gamma rays and displace an electron, which emits a photon on its return a lower orbital state. Some cameras also use photoelectric detectors, e.g., arranged in a spatial detection chamber to determine the position of an emitted photon, as well as circuitry to analyze the photons detected in the chamber to help produce an image.

In embodiments using an imaging moiety comprising a magnetic species, e.g., a paramagnetic atom, the imaging moiety can be detected by MR imaging, e.g., a magnetic resonance imaging system can be used. In such systems, a strong magnetic field can be used to align nuclear spin vectors of atoms, such as paramagnetic atoms at localized sites of lung tissue. The field can then be distributed by the paramagnetic atoms at such sites. As the nuclei return to equilibrium alignments, an image of lung tissue, e.g., localized sites of collapsed and/or sealed lung tissue, can be obtained.

Some embodiments of the present invention employ both imaging and volume-reducing aspects of the invention described herein. In some embodiments, the imaging moiety may be coupled to an adhering moiety that itself is coupled to a cross-linkable moiety and/or one or more other adhering moieties. In some embodiments, a second composition comprising an adhering moiety coupled to an imaging moiety can be used. In some embodiments, lung volume reduction, e.g., using glue compositions and/or methods described herein, may be preceded and/or followed by imaging, e.g., and the images compared, e.g., to determine the extent of collapse and/or sealing achieved in regions of selected damaged lung tissue.

Administration of a glue composition comprising an adhering moiety coupled to all and any of an imaging moiety, a cross-linkable moiety, a cross-linking activating moiety, other adhering moiety, and/or other moiety and/or agent, may be followed by washing. The term "washing" as used herein refers to administration of a washing moiety that can facilitate removal of an adhering moiety from lung tissue. For instance, a washing step may follow administration and imaging of a glue composition comprising an adhering moiety coupled to an imaging moiety to free up sites. Following washing, a glue composition comprising an adhering moiety coupled to a cross-linkable moiety and/or coupled to another adhering moiety may be administered to the subject, for example to achieve lung volume reduction by methods described herein. Washing moieties suitable for use in the present invention include, for example, soluble components of lung tissue to which adhering moieties can bind. The soluble components can compete with lung tissue components for binding with the adhering moieties. Preferably, the soluble components are modified so as to reduce and/or eliminate undesirable properties before administration to a subject. For example, a mutant elastase polypeptide may be used that can still bind to alpha-1 antitrypsin but that cannot degrade lung tissue or degrades lung tissue to a lesser extent than non-mutant elastase.

While preferred embodiments of the present invention have been shown and described herein, it will be obvious to those skilled in the art that such embodiments are provided by way of example only. Numerous variations, changes, and substitutions will now occur to those skilled in the art without departing from the invention, and it should be understood that various alternatives to the embodiments of the invention described herein may be employed in practicing the invention. It is intended that the following claims define the scope of the invention and that methods and compositions within the scope of these claims, along with their equivalents, are covered thereby.

All publications, patents, and patent applications mentioned in this specification are herein incorporated by reference to the same extent as if each individual publication, patent or patent application was specifically and individually indicated as being incorporated by reference.

What is claimed is:

1. A glue composition comprising:
   a first adhering moiety connected via an amide bond linkage to a first site on a coupling moiety which is a chemical linker; and
   a second adhering moiety which is connected via an amide bond to a second site on said coupling moiety, wherein said first and second adhering moieties adhere to different sites bearing elastase in a lung, and each adhering moiety is a member selected from the group consisting of alpha-1 antitrypsin, elafin, and a serpin, and wherein said chemical linker comprises two functional groups.

2. The glue composition according to claim 1, wherein at least one of said functional groups of the chemical linker is a carboxyl group, an ester group, or an amine group, or wherein said chemical linker comprises a lysine.

* * * * *